(12) United States Patent
Jeong et al.

(10) Patent No.: US 12,237,088 B2
(45) Date of Patent: Feb. 25, 2025

(54) CUSTOMIZED COSMETICS PROVISION SYSTEM AND OPERATING METHOD THEREOF

(71) Applicant: LG HOUSEHOLD & HEALTH CARE LTD., Seoul (KR)

(72) Inventors: Su Ra Jeong, Daejeon (KR); Jung A Kim, Daejeon (KR); Joon Oh Myoung, Daejeon (KR); Jong Sub Han, Daejeon (KR)

(73) Assignee: LG HOUSEHOLD & HEALTH CARE LTD., Seoul (KR)

( * ) Notice: Subject to any disclaimer, the term of this patent is extended or adjusted under 35 U.S.C. 154(b) by 0 days.

(21) Appl. No.: 18/196,816

(22) Filed: May 12, 2023

(65) Prior Publication Data

US 2023/0282366 A1  Sep. 7, 2023

Related U.S. Application Data

(62) Division of application No. 16/465,903, filed as application No. PCT/KR2017/007805 on Jul. 20, 2017, now Pat. No. 11,742,089.

(30) Foreign Application Priority Data

Dec. 1, 2016  (KR) .................. 10-2016-0163000
Dec. 6, 2016  (KR) .................. 10-2016-0165341

(51) Int. Cl.
*G16H 50/30*  (2018.01)
*A45D 44/00*  (2006.01)
(Continued)

(52) U.S. Cl.
CPC ............ *G16H 50/30* (2018.01); *A45D 44/00* (2013.01); *A61B 5/00* (2013.01); *G05B 15/02* (2013.01);
(Continued)

(58) Field of Classification Search
CPC .......... G16H 50/30; A45D 44/00; A61B 5/00; A61B 5/442; A61B 5/443; G05B 15/02; G06Q 30/06
See application file for complete search history.

(56) References Cited

U.S. PATENT DOCUMENTS 5,938,080 A    8/1999  Haaser et al.
8,527,365 B2   9/2013  Pak
(Continued)

FOREIGN PATENT DOCUMENTS

CN     1457467 A       11/2003
CN   101432748 A        5/2009
(Continued)

OTHER PUBLICATIONS

Young-Jun, System for producing customized individual cosmetics, 2015, note this is a machine translation of WO2015088079 ( Year: 2015).*

(Continued)

*Primary Examiner* — Robert E Fennema
*Assistant Examiner* — Yvonne Trang Follansbee
(74) *Attorney, Agent, or Firm* — Birch, Stewart, Kolasch & Birch, LLP

(57) ABSTRACT

Discussed is a customized cosmetics provision system including a diagnosis device for diagnosing a skin condition, recommending customized cosmetics based on a diagnosis result of the skin condition, and transmitting information on the recommended customized cosmetics to a manufacturing apparatus, and the manufacturing apparatus that receives information on the customized cosmetics from the diagnosis device and provides the customized cosmetics based on the received information on the customized cosmetics. The diagnosis device can output a message to re-diagnose the skin condition when an environmental condition for diag- (Continued)

nosing the skin condition do not meet a predetermined condition.

20 Claims, 13 Drawing Sheets

(51) Int. Cl.
  *A61B 5/00* (2006.01)
  *G05B 15/02* (2006.01)
  *G06Q 30/06* (2023.01)
(52) U.S. Cl.
  CPC .............. *G06Q 30/06* (2013.01); *A61B 5/442* (2013.01); *A61B 5/443* (2013.01)

(56) References Cited

U.S. PATENT DOCUMENTS

| | | | |
|---|---|---|---|
| 8,693,768 B1 * | 4/2014 | LaForgia | G06Q 30/0621 382/165 |
| 2003/0065525 A1 | 4/2003 | Giacchetti et al. | |
| 2008/0080766 A1 | 4/2008 | Payonk et al. | |
| 2008/0311061 A1 | 12/2008 | Heuer | |
| 2009/0076639 A1 * | 3/2009 | Pak | G06Q 10/08 700/106 |
| 2011/0247718 A1 * | 10/2011 | Samain | B01F 35/2205 141/94 |
| 2012/0123759 A1 * | 5/2012 | Cho | G06T 19/20 703/6 |
| 2012/0302817 A1 | 11/2012 | Nishiuchi et al. | |
| 2014/0267664 A1 | 9/2014 | Gross et al. | |
| 2015/0057551 A1 * | 2/2015 | Chou | A61B 5/1032 600/476 |
| 2015/0356661 A1 | 12/2015 | Rousay | |
| 2016/0107133 A1 | 4/2016 | Sugino et al. | |
| 2017/0322070 A1 | 11/2017 | Castellari et al. | |

FOREIGN PATENT DOCUMENTS

| | | | | |
|---|---|---|---|---|
| DE | 202004011856 U1 | | 1/2005 | |
| JP | 2001-104050 A | | 4/2001 | |
| JP | 2002-501463 A | | 1/2002 | |
| JP | 2002-183604 A | | 6/2002 | |
| JP | 2003-252721 A | | 9/2003 | |
| JP | 2003-310350 A | | 11/2003 | |
| JP | 2006-110075 A | | 4/2006 | |
| JP | 2011-62326 A | | 3/2011 | |
| JP | 2011-98187 A | | 5/2011 | |
| JP | 2011-115393 A | | 6/2011 | |
| JP | 2011-173810 A | | 9/2011 | |
| JP | 2013-226286 A | | 11/2013 | |
| JP | 2016-146923 A | | 8/2016 | |
| JP | 2016-523574 A | | 8/2016 | |
| KR | 10-2000-0030538 A | | 6/2000 | |
| KR | 10-0708319 B1 | | 4/2007 | |
| KR | 10-2012-0066286 A | | 6/2012 | |
| KR | 10-1299848 B1 | | 9/2013 | |
| KR | 10-2014-0012386 A | | 2/2014 | |
| KR | 10-2014-0072685 A | | 6/2014 | |
| KR | 10-2014-0099946 A | | 8/2014 | |
| KR | 10-1490987 B1 | | 2/2015 | |
| KR | 10-2015-0093332 A | | 8/2015 | |
| KR | 10-2015-0098130 A | | 8/2015 | |
| KR | 20150098130 A | * | 8/2015 | ......... G06Q 30/0282 |
| KR | 10-2016-0036791 A | | 4/2016 | |
| KR | 10-2018-0007500 A | | 1/2018 | |
| KR | 20180007500 A | * | 1/2018 | ............ A45D 44/005 |
| WO | WO02/069215 A1 | | 9/2002 | |
| WO | WO 2014/029509 A1 | | 2/2014 | |
| WO | WO 2015/004903 A1 | | 1/2015 | |
| WO | WO 2015/0880879 A1 | | 6/2015 | |
| WO | WO-2015088079 A1 | * | 6/2015 | ......... G06F 19/3418 |

OTHER PUBLICATIONS

Hwang Jeong, Apparatus for manufacturing customized cosmetics, 2018, note this is a machine translation KR20180007500 (Year: 2018).*

Joo-Yeon, Apparatus and Method for recommending cosmetic based on user skin information, 2015, note this is a maching translation of KR20150098130A (Year: 2015).*

International Search Report (PCT/ISA/210) issued in PCT/KR2017/007805, mailed on Nov. 17, 2017.

* cited by examiner

CUSTOMIZED COSMETICS PROVISION SYSTEM AND OPERATING METHOD THEREOF

CROSS-REFERENCE TO RELATED APPLICATIONS

This application is a Divisional application of U.S. patent application Ser. No. 16/465,903, filed on May 31, 2019, which was filed as the National Phase of PCT International Application No. PCT/KR2017/007805, filed on Jul. 20, 2017, which claims priority under 35 U.S.C. 119(a) to Patent Application Nos. 10-2016-0163000, filed in the Republic of Korea on Dec. 1, 2016 and 10-2016-0165341, filed in the Republic of Korea on Dec. 6, 2016, the entire contents of all these applications being hereby expressly incorporated by reference into the present application.

BACKGROUND OF THE DISCLOSURE

Field

The present invention relates to a customized cosmetics provision system and an operating method thereof, and more particularly, to a customized cosmetics provision system for providing customized cosmetics appropriate for a skin condition of a user by diagnosing the skin condition of the user, and an operating method thereof.

Discussion of the Related Art

Recently, the kinds of cosmetics have become very diverse according to the development of beauty industry. Specifically, there are cosmetics for dry skin, neutral skin and oily skin, and the like according to a skin type, cosmetics such as beige and pink beige according to a skin color, and various cosmetics for whitening, for improving wrinkles, for blocking ultraviolet rays, and the like according to functions.

However, since each user has different skin features or skin troubles, it is limited to meet the needs of all users by providing of various cosmetics. That is, since ingredients and contents of a cosmetic material may be required differently depending on a skin condition of each user, it is difficult to provide cosmetics that may meet the needs of all users.

SUMMARY OF THE DISCLOSURE

The present invention is directed to providing a customized cosmetics provision system for providing customized cosmetics appropriate for a skin condition of an individual user by diagnosing the skin condition of the user.

The present invention is directed to providing a diagnosis device for diagnosing a skin condition of a user.

The present invention is directed to providing a skin management server for recommending customized cosmetics, based on a diagnosis result of a skin condition of a user.

The present invention is directed to providing a manufacturing apparatus for manufacturing customized cosmetics based on ingredients and contents or a mixing ratio of a cosmetic material.

A customized cosmetics provision system according to an embodiment of the present invention includes a diagnosis device for diagnosing a skin condition, recommending customized cosmetics based on a diagnosis result of the skin condition, and transmitting information on the recommended customized cosmetics to a manufacturing apparatus, and the manufacturing apparatus that receives information on the customized cosmetics from the diagnosis device and provides the customized cosmetics based on the received information on the customized cosmetics.

The customized cosmetics may include cosmetics manufactured with at least one cosmetic material at a predetermined mixing ratio, and commercial cosmetics manufactured already.

When the recommended customized cosmetics are manufactured with at least one cosmetic material at a predetermined mixing ratio, the manufacturing apparatus may manufacture the customized cosmetics based on ingredients of the received cosmetic material and the mixing ratio.

The diagnosis device may include a mobile terminal capable of diagnosing a skin condition and a skin condition diagnosis device provided in a cosmetics sales place.

When the diagnosis device is the mobile terminal, the customized cosmetics may be provided at a cosmetics sales place closest to a current location of the mobile terminal.

When the diagnosis device is the mobile terminal, the diagnosis device may receive an input signal inputting a location, and the customized cosmetics may be provided at a cosmetics sales place closest to an input location according to the input signal.

When the diagnosis device is the mobile terminal, the diagnosis device may receive an input signal inputting a delivery address, and the customized cosmetics may be provided at a delivery address input according to the input signal.

When the diagnosis device is a skin condition diagnosis device provided at a cosmetics sales place, the customized cosmetics may be provided at a cosmetics sales place in which the skin condition is diagnosed.

The diagnosis device may determine purchasing intention of a user corresponding to the recommended customized cosmetics, and when it is determined that there is the purchasing intention of the user corresponding to the customized cosmetics, may transmit information on the customized cosmetics to the manufacturing apparatus.

The diagnosis device may receive a correction signal that changes some or all of the recommended customized cosmetics.

A diagnosis device for providing customized cosmetics according to an embodiment of the present invention may include a measurement unit for measuring a skin condition, an analysis unit for diagnosing the measured skin condition, a control unit for recommending customized cosmetics based on a diagnosis result of the skin condition, and a communication unit for transmitting information on the recommended customized cosmetics to a manufacturing apparatus.

The skin condition may include at least one of skin color, moisture content in skin, sebum content in skin, elasticity, wrinkles, presence of pigmentation, amount of pores, keratin, skin texture, sensitivity, skin type, and skin trouble.

The diagnosis device may further include a display unit for displaying question contents related to the skin condition, and an input unit for receiving a response signal corresponding to the displayed question contents, and the analysis unit may diagnose the skin condition based on the question contents and the response signal.

The analysis unit may analyze the skin condition in consideration of the question contents, the response signal, and the measured skin condition, respectively or together.

The display unit may further display a diagnosis result of the skin condition.

The control unit may determine purchasing intention of a user corresponding to the recommended customized cosmetics, and when it is determined that there is the purchasing intention of the user corresponding to the customized cosmetics, may transmit information on the customized cosmetics to the manufacturing apparatus.

A skin management server for providing customized cosmetics according to an embodiment of the present invention includes a communication unit for receiving a diagnosis result of a first skin condition and information on first customized cosmetics corresponding to the diagnosis result of the first skin condition, a storage unit for mapping and storing the diagnosis result of the first skin condition and the information on the first customized cosmetics, and a control unit for obtaining information on second customized cosmetics based on the stored diagnosis result of the first skin condition and the information on the first customized cosmetics when receiving a diagnosis result of a second skin condition.

The communication unit may transmit the information on the second customized cosmetics to a manufacturing apparatus.

A manufacturing apparatus for providing customized cosmetics according to an embodiment of the present invention includes at least one cartridge for containing a cosmetic material, a cartridge support for accommodating the cartridge, a motor mounted on one side of the cartridge support for moving a compression member, the compression member moved by the motor for discharging the cosmetic material contained in the cartridge when inserted into the cartridge, and a cosmetics container for accommodating the discharged cosmetic material.

The cartridge support may be rotated clockwise or counterclockwise.

The cartridge may include a cartridge stopper formed with a surface to which the compression member applies pressure, and a material injection hole through which the cosmetic material contained in the cartridge is discharged as pressure is applied to the cartridge stopper.

The manufacturing apparatus may further include a sensor for measuring a weight of a cosmetics container.

In a customized cosmetics providing application executed in a mobile terminal according to an embodiment of the present invention, it is possible to execute a function for diagnosing a skin condition, a function for recommending customized cosmetics based on a diagnosis result of the skin condition, and a function for transmitting information on the recommended customized cosmetics to a manufacturing apparatus.

The customized cosmetics providing application may further include a function for modifying the information on the customized cosmetics.

The customized cosmetics providing application may further include a function for storing the information on the customized cosmetics.

The customized cosmetics providing application may further include a function for determining a user's purchasing intention corresponding to the customized cosmetics.

According to various embodiments of the present invention, customized cosmetics appropriate for a skin condition of each user are provided, thereby effectively solving concerns of the user using the cosmetics, and enhancing the satisfaction and reliability of the cosmetics.

According to various embodiments of the present invention, there is an advantage that the user can be easily provided with customized cosmetics without visiting for a cosmetics sales place.

BRIEF DESCRIPTION OF THE DRAWINGS

The present invention will become more fully understood from the detailed description given hereinbelow and the accompanying drawings which are given by way of illustration only, and thus are not limitative of the present invention.

DETAILED DESCRIPTION OF THE EMBODIMENTS

Figure 1:
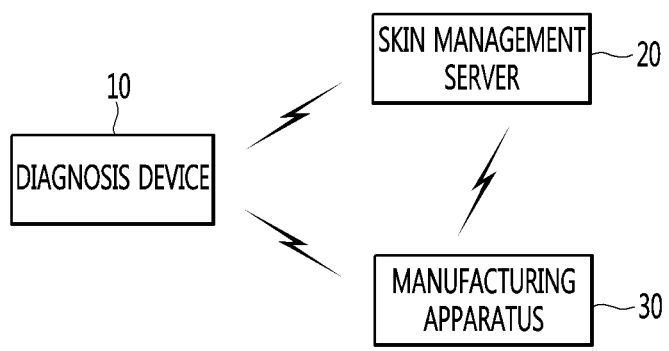
FIG. 1 is a view illustrating a customized cosmetics provision system according to an embodiment of the present invention.

Hereinafter, embodiments will be described in detail with reference to the accompanying drawings, however, the same components are designated by the same reference numerals, and repeated description thereof will be omitted. Suffixes "module" and "part" for elements used in the following descriptions are given or used just for convenience in writing the specification, and do not have meanings or roles distinguishable between them. In addition, in describing embodiments of the present disclosure, when detailed description of a known function is deemed to unnecessarily blur the gist of the present disclosure, the detailed description will be omitted. Further, accompanying drawings are only for easily understanding embodiments disclosed in the present disclosure, and the technical spirit disclosed in the present disclosure are not limited by the accompanying drawings, and it should be understood that the present invention includes all modifications, equivalents, and alternatives falling within the spirit and scope of the claims.

It should be understood that, although the terms first, second, and the like may be used herein to describe various elements, these elements are not limited by these terms. The terms are only used to distinguish one element from another.

It should be understood that, when an element is referred to as being "connected" or "coupled" to another element, the element may be directly connected or coupled to the other element or intervening elements may be present. In contrast, when an element is referred to as being "directly connected" or "directly coupled" to another element, there are no intervening elements present.

Elements referred to in singular may be number one or more, unless the context clearly indicates otherwise.

It should be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Hereinafter, a customized cosmetics provision system according to an embodiment of the present invention will be described with reference to FIGS. 1 to 15.

FIG. 1 is a view illustrating a customized cosmetics provision system according to an embodiment of the present invention.

As shown in FIG. 1, the customized cosmetics provision system may include at least one of a diagnosis device 10, a skin management server 20, and a manufacturing apparatus 30. The diagnosis device 10, the skin management server 20, and the manufacturing apparatus 30 may provide customized cosmetics to a user by transmitting and receiving signals to and from each other.

Specifically, the diagnosis device 10 may measure a user's skin condition.

According to one embodiment of the present invention, the diagnosis device 10 may recommend customized cosmetics based on the measured skin condition.

According to another embodiment of the present invention, the skin management server 20 may recommend customized cosmetics based on a result of measuring the skin condition by the diagnosis device 10.

However, it is merely illustrative, and the customized cosmetics may be recommended in at least one of the diagnosis device 10, the skin management server 20, and the manufacturing apparatus 30. For example, the diagnosis device 10 analyzes the customized cosmetics according to an inquiry method described later, and the skin management server 20 analyzes the customized cosmetics according to a user's skin condition, and thus it is possible to recommend the customized cosmetics. Therefore, it is appropriate that a method of recommending the customized cosmetics is not limited to the described above.

The manufacturing apparatus 30 may manufacture to provide the recommended cosmetics to the user based on a result of recommending the customized cosmetics.

Figure 2:
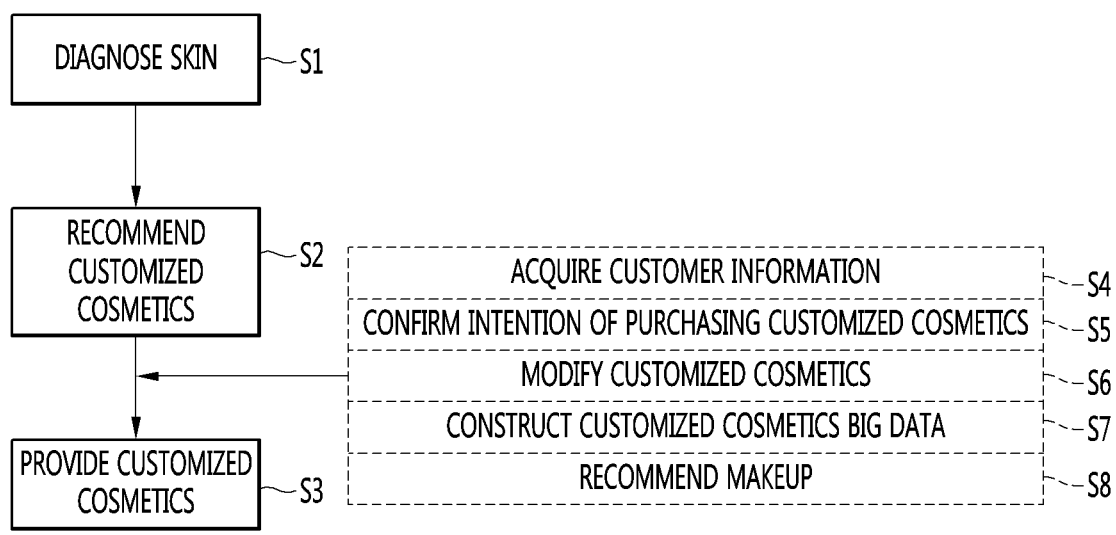
FIG. 2 is a flowchart schematically illustrating a customized cosmetics provision system according to an embodiment of the present invention.

FIG. 2 is a flowchart schematically illustrating a customized cosmetics provision system according to an embodiment of the present invention.

As shown in FIG. 2, the customized cosmetics provision system according to an embodiment of the present invention may be composed of a step of diagnosing skin (S1), a step of recommending customized cosmetics (S2), and a step of providing the cosmetics (S3).

According to one embodiment, the customized cosmetics provision system may omit some of the steps listed above.

According to another embodiment, the customized cosmetics provision system may further include a new step except for the steps listed above. For example, as shown in FIG. 2, the customized cosmetics provision system may further include at least one of a step of obtaining customer information (S4), a step of confirming intention of purchasing the customized cosmetics (S5), a step of modifying the customized cosmetics (S6), a step of constructing big data of the customized cosmetics (S7), and a step of recommending makeup (S8). However, it is merely illustrative, and the new step is not limited thereto.

Each step of configuring the customized cosmetics provision system may be performed by different devices.

According to one embodiment, the step of diagnosing skin (S1) and the step of recommending customized cosmetics (S2) may be performed by the diagnosis device 10, and the step of manufacturing customized cosmetics (S3) may be performed by the manufacturing apparatus 30.

According to another embodiment, the step of diagnosing skin (S1) may be performed by the diagnosis device 10, the step of recommending customized cosmetics (S2) may be performed by the skin management server 20, and the step of manufacturing customized cosmetics (S3) may be performed the manufacturing apparatus 30. However, it is merely illustrative, and two or more steps may be performed by one apparatus.

Hereinafter, each step of configuring a customized cosmetics provision system will be described in detail.

First, the step of diagnosing skin (S1) of the customized cosmetics provision system according to the present invention will be described.

According to one embodiment, the step of diagnosing skin (S1) may be performed by the diagnosis device 10. Next, referring to FIG. 3, the diagnosis device 10 according to an embodiment of the present invention will be described.

Figure 3:
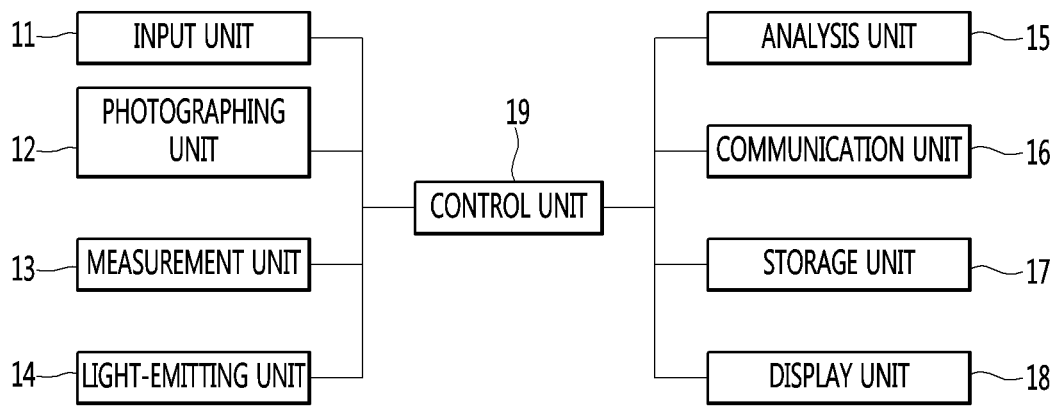
FIG. 3 is a block diagram for describing a diagnosis device according to an embodiment of the present invention.

FIG. 3 is a block diagram for describing a diagnosis device according to an embodiment of the present invention.

The diagnosis device 10 may include at least one of an input unit 11, a photographing unit 12, a measurement unit 13, a light-emitting unit 14, an analysis unit 15, a communication unit 16, a storage unit 17, a display unit 18, and a control unit 19.

The input unit 11 may receive a signal for inputting data required for diagnosing a skin condition.

The input unit 11 may include a keypad, a dome switch, a touch pad (static pressure/electrostatic), a jog wheel, a jog switch, and the like.

The photographing unit 12 may photograph a region required for analysis of a user's skin condition. For example, the photographing unit 12 may photograph a user's skin region, a user's entire face region, and the like.

The measurement unit 13 may measure data required for analysis of a skin condition. For example, the measurement unit 13 may measure light reflected from a skin region, or skin color, or moisture content of skin, or pore depth, or ambient temperature/humidity around the diagnosis device 10, or the like.

The measurement unit 13 may include an optical sensor, an imaging sensor, a moisture measuring sensor, a temperature sensor, and the like.

The light-emitting unit 14 may emit light required for diagnosing a skin condition.

The analysis unit 15 may diagnose a skin condition based on data obtained through at least one of the input unit 11, the photographing unit 12, and the measurement unit 13, and may recommend customized cosmetics based on a diagnosis result of the skin condition.

In the present invention, the skin condition may refer to current skin features of the user. More specifically, the skin condition may include skin color, moisture content in skin, sebum content in skin, elasticity of skin, wrinkles of skin, sensitivity, skin staining, pores, UV exposure, sebum, symmetry, cleansing, color makeup condition, keratin, skin texture, skin type, skin stress according to hazardous environmental exposures and cosmetic habits, etc. However, it is merely illustrative and an element representing skin features of the user may be included all in the skin condition.

According to one embodiment, the analysis unit 15 may diagnose an objective skin condition regardless of a user's age.

According to another embodiment, the analysis unit 15 may diagnose an objective skin condition and a skin condition in consideration of a user's age. For example, the analysis unit 15 may analyze that the objective skin condition of the user is normal, but the skin condition compared to the user's age is good. However, it is merely illustrative, but is not limited thereto.

The communication unit 16 may transmit and receive at least one piece of data required for providing customized cosmetics to and from an external device. For example, the communication unit 16 may transmit information on the customized cosmetics to the external device.

The communication unit 16 may transmit data to or receive data from an external device using a wired/wireless communication module supporting wired/wireless communication technology. Here, the wired communication technology may include universal serial bus (USB) communication, etc., and the wireless communication technology may include wireless LAN (WLAN), Wi Fi, wireless broadband (Wibro), world interoperability for microwave access (Wimax), high speed downlink packet access (HSDPA), IEEE 802.16, long term evolution (LTE), wireless mobile broadband service (WMBS), and the like.

The storage unit 17 may store data required for diagnosing a skin condition. For example, the storage unit 17 may store a table in which colors of cosmetics corresponding to a measurement value are mapped, a table in which the number of wrinkles on skin and the age of the skin are mapped, and the like.

The storage unit 17 may store information required for recommending customized cosmetics. The storage unit 17 may store information on customized cosmetics that may be recommended according to a diagnosis result of the skin condition.

The display unit 18 may display a diagnosis result of the skin condition. Alternatively, the display unit 18 may display question contents and response contents when diagnosing the skin condition by an inquiry method.

The display unit 18 may display information on customized cosmetics recommended based on the diagnosis result of the skin condition.

The control unit 19 may control overall operations required for providing customized cosmetics. The control unit 19 may control individual operations or combined operations of each component constituting the diagnosis device 10.

The operation of each component described above is illustrative, and each component may perform various operations required for diagnosing the skin condition.

The diagnosis device 10 for diagnosing the skin condition, may include a personal mobile terminal capable of diagnosing the skin condition and a skin diagnosis device provided in a cosmetics sales place. For example, the diagnosis device 10 may include a smart phone, a mobile phone, a cellular phone, a smart pad, a personal digital assistant (PDA), a tablet, a laptop, a desktop PC, a facial tester, a skin meter, a tone meter, an oil meter, a moisture meter, a keratin meter, an elasticity meter, etc.

The diagnosis device 10 according to an embodiment of the present invention may diagnose, measure, or analyze a skin condition for each user to provide customized cosmetics to the user.

Hereinafter, a method of diagnosing a skin condition by the diagnosis device 10 in a step of diagnosing skin (S1) according to various embodiments of the present invention will be described.

A skin diagnosis method according to a first embodiment of the present invention uses a gradation of a skin image, and is as follows.

The photographing unit 12 of the diagnosis device 10 may photograph a skin region to obtain a skin image. The analysis unit 15 of the diagnosis device 10 may separate the obtained image into a plurality of skin color planes which are R-plane, G-plane and B-plane to diagnose a skin condition.

According to one embodiment, the analysis unit 15 may calculate an average gradation of a skin image by extracting data of each separated color plane. Meanwhile, the storage unit 17 of the diagnosis device 10 may store a plurality of gradations and a gradation table in which skin condition information corresponding to each gradation is mapped. The analysis unit 15 of the diagnosis device 10 may obtain a gradation matching the calculated average gradation from the stored gradation table to diagnose a skin condition of a user.

According to another embodiment, the analysis unit 15 of the diagnosis device 10 of may extract only one color plane of a plurality of separated color planes (R-plane, G-plane and B-plane), and may calculate a variance of gray levels of the extracted color plane. Meanwhile, the storage unit 17 of the diagnosis device 10 may store an age curve mapping a gray level variance and a skin age. Therefore, the analysis unit 15 may obtain the skin age corresponding to the calculated gray level variance from the age curve to diagnose a skin condition.

According to still another embodiment, the analysis unit 15 of the diagnosis device 10 may convert separated color planes (R-plane, G-plane and B-plane) into standard RGB (sRGB). sRGB is a color space used in an HDTV system, and when converted to the sRGB, the same color reproduction result may be obtained from a monitor, a camera, and a scanner. The analysis unit 15 of the diagnosis device 10 may model a color distribution of standard R, G and B components by the Gaussian probability distribution having sRGB estimated parameters. Here, the estimated parameters may be an estimated standard deviation obtained through skin images. The analysis unit 15 may diagnose a skin condition such as a skin type using the modeled R, G and B components.

A skin diagnosis method according to a second embodiment of the present invention uses a method photographing a skin region by irradiating light therein, and is as follows.

According to one embodiment, the light-emitting unit 14 of the diagnosis device 10 irradiates excitation light to a skin region with a predetermined area, and the measurement unit 13 of the diagnosis device 10 may detect magnetic fluorescence generated by the irradiated excitation light. The analysis unit 15 of the diagnosis device 10 may generate a fluorescence image of a skin using the detected magnetic fluorescence, and may analyze a distribution pattern of fluorescence intensity through the generated fluorescence image of the skin to diagnose the skin condition of the user.

According to another embodiment, the light-emitting unit 14 of the diagnosis device 10 may irradiate light to a skin region to be diagnosed. At this time, the light irradiated in the skin region by the light-emitting unit 14 may be light of spectral characteristics having peaks different in influence of absorption by melanin and hemoglobin in wavelength bands of green (G) and blue (B). The diagnosis device 10 may further include a filter (not shown) transmitting only each of the wavelength bands of R, G, and B, and the photographing unit 12 may photograph reflected light passing through each filter and reflected from the skin region. The analysis unit 15 may output image signals photographed through each of the wavelength bands of R, G, and B to diagnose a skin condition such as skin pigmentation, area, and the like.

A skin diagnosis method according to a third embodiment of the present invention uses polarized light, and is as follows.

The photographing unit 12 of the diagnosis device 10 may photograph a skin image using a camera equipped with at least two polarizing filters.

According to one embodiment, the measurement unit 13 of the diagnosis device 10 may calculate reflection light data varying according to a change of a relative angle between two polarizing filters to obtain internal reflection light of skin or external reflection light of skin. Meanwhile, the storage unit 17 of the diagnosis device 10 may store a skin level table according to a reflected light value on the skin, and the analysis unit 15 may compare the obtained internal reflected light of the skin or the external reflected light of the skin with the stored skin level table to diagnose a skin condition of a user.

According to another embodiment, the measurement unit 13 of the diagnosis device 10 may photograph a cross-polarized image and a parallel-polarized image of skin, and may obtain a surface reflected light image corresponding to a difference between the photographed cross-polarized image and the parallel-polarized image to diagnose a skin condition such as a glossy index.

A skin diagnosis method according to a fourth embodiment of the present invention uses a predetermined formula, and is as follows.

According to one embodiment, the storage unit 17 of the diagnosis device 10 may store at least one formula related to diagnosis of a skin condition. The photographing unit 12 or the measurement unit 13 of the diagnosis device 10 may obtain data related to the skin condition, and the analysis unit 15 may apply the obtained data to the predetermined formula to diagnose the skin condition. For example, the measurement unit 13 of the diagnosis device 10 may measure light reflectivity of a skin region, a mucosa region or a connective tissue region. The analysis unit 15 may obtain L representing brightness through the measured light reflectivity, a representing a closer color of red and green, and b representing a closer color of yellow and blue. The analysis unit 15 may apply the obtained L, a, and b to the predetermined formula. The predetermined formula may be (Lmax−L)×a, (Lmax−L)×b, but it is merely illustrative. The analysis unit 15 may apply the obtained L, a, and b to the predetermined formula to diagnose a skin condition such as skin color and colors of red spots.

According to another embodiment, the measurement unit 13 of the diagnosis device 10 may obtain image data of a first skin region captured with incident white light, and may obtain image data of a second skin region captured with incident polarized light. The analysis unit 15 of the diagnosis device 10 may convolute the obtained image data of the first skin region and the image data of the second skin region, and may compare two convolutional extreme locations generated by convolution to diagnose a skin condition such as a skin type.

A skin diagnosis method according to a fifth embodiment of the present invention uses a gray scale of a skin image, and is as follows.

According to one embodiment, the photographing unit 12 of the diagnosis device 10 may obtain a skin image by photographing a skin region. The analysis unit 15 of the diagnosis device 10 may calculate a gray scale value of the obtained skin image, and may calculate the number of particles of pixels belonging to a range from a predetermined gray scale value to a maximum gray scale value. The analysis unit 15 of the diagnosis device 10 may diagnose a skin condition such as moisture content of a skin region using the calculated number of particles.

A skin diagnosis method according to a sixth embodiment of the present invention is a method for determining a skin color, and is as follows.

According to one embodiment, the storage unit 17 of the diagnosis device 10 may store skin color type information including a plurality of skin colors. The measurement unit 13 of the diagnosis device 10 may measure skin color of a user, and the analysis unit 15 may obtain a color similar to the measured skin color from the stored skin color type information to diagnose a skin condition such as a skin color type of a user.

According to another embodiment, the photographing unit 12 of the diagnosis device 10 may further photograph a reference color chart together with a skin region. While the photographing unit 12 photographs the skin region and the reference color chart, the light-emitting unit 14 may irradiate light of the same intensity to the skin region and the reference color chart. In particular, the diagnosis device 10 may further include an external light blocking member (not shown) to block light other than the light irradiated from the light-emitting unit 14. The analysis unit 15 may obtain the same color as the color of the photographed skin region from the reference color chart to diagnose a skin condition such as a skin color type. In this case, there is an advantage that the skin region and the reference color chart may be photographed under the same condition to more accurately diagnose the skin condition.

A skin diagnosis method according to a seventh embodiment of the present invention uses a pigmented region of skin, and is as follows.

According to one embodiment, the photographing unit 12 of the diagnosis device 10 may photograph a skin region to obtain a skin image. The analysis unit 15 of the diagnosis device 10 may apply a weight to data of the obtained image to derive a contour of a pigmentation region. The analysis unit 15 of the diagnosis device 10 may analyze a shape of the pigmentation region, a location of the pigmentation region, a size and number of the pigmentation region, and the like from the contour of the pigmentation region to diagnose a skin condition of a user.

According to another embodiment, the photographing unit 12 of the diagnosis device 10 may obtain a skin image by photographing a skin region with a white light or the like, and the analysis unit 15 may detect an edge line of a portion having a higher density than a predetermined threshold value by processing a color signal having a predetermined wavelength among color signals included in the obtained skin image to obtain a pigmentation region. The analysis unit 15 of the diagnosis device 10 may diagnose a skin condition of a user through the obtained pigmentation region.

According to still another embodiment, the photographing unit 12 of the diagnosis device 10 may photograph a skin region to obtain a skin image. The measurement unit 13 of the diagnosis device 10 may resolve at least one or more color shadings of a predetermined size in the skin image. The analysis unit 15 may obtain skin color information in color shading, and may calculate a color shading index through the obtained color information. The color shading index according to the color information may be set by default or may be set by a user input. For example, when the color information is white, the color shading index may be 0 to 4, when the color information is yellow, the color shading index may be 5 to 7, when the color information is red, the color shading index may be 8 to 9, but it is merely illustrative and is not limited thereto. The analysis unit 15 may diagnose a skin condition such as dullness degree of skin through the calculated color shading index.

A skin diagnosis method according to an eighth embodiment of the present invention is a method for determining a sebum content in skin, and is as follows.

The photographing unit 12 of the diagnosis device 10 may photograph a fluorescence image of a skin region. The analysis unit 15 of the diagnosis device 10 may extract a bright-white fluorescence point from the fluorescence image, and may recognize a distribution of the extracted bright-white fluorescence point as a sebum distribution of the skin. Therefore, the analysis unit 15 may obtain an area ratio or intensity of the bright-white fluorescence point, etc. to diagnose a skin condition such as a sebum distribution, sebum content, and the like of a user.

A skin diagnosis method according to a ninth embodiment of the present invention is a method for determining a wrinkle state of skin, and is as follows.

The photographing unit 12 of the diagnosis device 10 may obtain a skin image by photographing a skin region. The analysis unit 15 of the diagnosis device 10 may extract a linear text image for each of a plurality of predetermined angles from the skin image. The analysis unit 15 may extract intensity of a linear component at each predetermined angle in the linear text image to diagnose a skin condition such as the number of wrinkles on the skin and the wrinkle sensitivity.

A skin diagnosis method according to a tenth embodiment of the present invention is a method for determining a pore state of skin, and is as follows.

The photographing unit 12 of the diagnosis device 10 may photograph a pore optical coherence tomographic image of skin. The analysis unit 15 may extract a contour of pores from the pore optical coherence tomographic image, and may measure a distance from a skin surface to the narrowest portion in a depth direction of the pores. The analysis unit 15 may measure strength of the pores in proportion to the strength of the pores from the distance from the skin surface to the narrowest portion of the pores for each pore. The analysis unit 15 may diagnose a skin condition such as a distribution of the pores and a depth of the pores through the contour of the pores and the strength of the pores.

A skin diagnosis method according to an 11th embodiment of the present invention uses an inquiry method, and is as follows.

The display unit 18 of the diagnosis device 10 may output a skin-related question. For example, question content refers to content required for diagnosing a skin condition including a lifestyle such as a user's wake-up time/bedtime, a user's age, type of cosmetics used by a user, a user's occupation, makeup habits, a degree of harmful environmental exposure, and the like. However, it is merely illustrative, and is not limited thereto. Displayed question content may be updated periodically. The input unit 11 may receive a response signal corresponding to the displayed question content. The display unit 18 may further display response content received via the response signal together with the question content.

According to one embodiment, the analysis unit 15 may analyze a response signal received from a user based on data stored in the storage unit 17 to diagnose a skin condition of the user.

According to another embodiment, the communication unit 16 may transmit a response signal received from a user to the skin management server 20, and the skin management server 20 may diagnose a skin condition of the user based on the transmitted data. The skin management server 20 may transmit the analyzed skin condition of the user to the diagnosis device 10, and the communication unit 16 of the diagnosis device 10 may receive the analyzed skin condition of the user.

A skin diagnosis method according to a 12th embodiment of the present invention is a method in consideration of a surrounding environment to diagnose a skin condition, and is as follows.

The measurement unit 13 may detect surrounding environmental conditions. For example, the surrounding environmental conditions may include temperature, humidity, etc. of a space in which the diagnosis device 10 is located. However, it is merely illustrative, and is not limited thereto.

Meanwhile, the control unit 19 may set a reference of environmental conditions for accurate analysis of the skin condition. For example, the control unit 19 may set a reference temperature to 20 degrees, and a reference humidity to 80% on the basis of the environmental condition, but it is merely illustrative, and is not limited thereto.

When the measurement unit 13 of the diagnosis device 10 measures the skin condition of the user such as moisture content in skin, elasticity of skin and sebum in skin, the analysis unit 15 may correct the measured skin condition in consideration of the detected environmental conditions. Specifically, when the temperature measured through the measurement unit 13 is 20 degrees, and the humidity is 50%, it is possible to make a correction to increase the measured moisture content in the skin by 30% by calculating the humidity 30% which is a difference between the surrounding environmental conditions and the reference of the surrounding environmental conditions.

Thus, the diagnosis device 10 may more accurately diagnose the skin condition of the user by correcting the measured skin condition in consideration of the surrounding environment.

Each of the embodiments described above is illustrative, and the diagnosis device 10 may also diagnose the skin condition through another method except the skin diagnosis method described above.

In addition, each of the embodiments of the diagnostic method described above may be performed independently, or a plurality of embodiments may be combined. For example, the diagnosis device 10 may combine an analysis result of a skin image photographed by the photographing unit 12 with the analysis of the response signal received by the input unit 11 in the inquiry method to diagnose the skin condition of the user. It is illustrative, and the diagnosis device 10 may combine one embodiment or two or more embodiments to diagnose the skin condition of the user.

In addition, a plurality of the diagnosis devices 10 may diagnose the skin condition. Specifically, a first diagnosis device 10 may photograph a user's skin and a second diagnosis device 10 may display a question related to a skin condition and receive a response to diagnose the skin condition.

The diagnosis device 10 may further determine whether the obtained image or skin information through the photographing unit 12 or the measurement unit 13 is appropriate for diagnosing a skin condition before diagnosing the skin condition. For example, the photographing unit 12 of the diagnosis device 10 obtains brightness of a photographed skin image, and when the obtained brightness is less than or equal to a predetermined reference, may determine that diagnosing the skin condition is inappropriate. In addition, the display unit 18 may output a message to measure a skin condition again to measure the skin condition again. Accordingly, there is an advantage that it is possible to prevent the skin condition from being erroneously measured due to a dark surrounding environment, a dry surrounding environment, or the like.

Next, a step of recommending customized cosmetics (S2) of a customized cosmetics provision system according to the present invention will be described.

The step of recommending the customized cosmetics (S2) according to an embodiment of the present invention may be a step of recommending appropriate cosmetics to the user based on the obtained data in the previously performed skin diagnosis step (S1).

According to one embodiment, the communication unit 16 of the diagnosis device 10 may transmit a diagnostic result of a skin condition to the skin management server 20 so that the skin management server 20 may recommend customized cosmetics.

Next, the skin management server 20 according to an embodiment of the present invention will be described with reference to FIG. 4.

Figure 4:
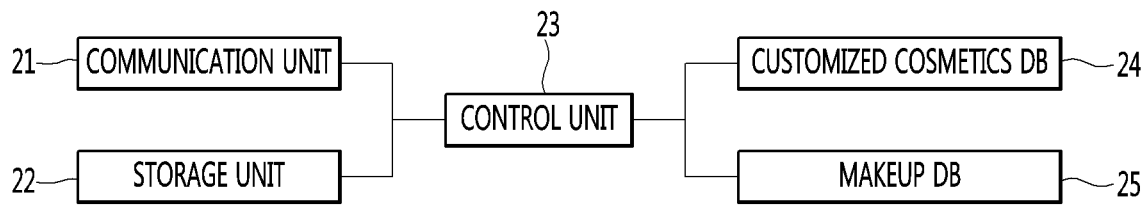
FIG. 4 is a block diagram for describing a skin management server according to an embodiment of the present invention.

FIG. 4 is a block diagram for describing a skin management server according to an embodiment of the present invention.

The skin management server 20 may include at least one of a communication unit 21, a storage unit 22, a control unit 23, a customized cosmetics DB 24, and a makeup DB 25.

The communication unit 21 may transmit and receive data required for providing customized cosmetics to and from the diagnosis device 10 or the manufacturing apparatus 30. For example, the communication unit 21 may transmit/receive data related to diagnosis of a skin condition to/from the diagnosis device 10, and may transmit/receive data related to the customized cosmetics to the manufacturing apparatus 30. In addition, the communication unit 21 may transmit and receive data related to the customized cosmetics to and from the diagnosis device 10.

The communication unit 21 is similar to the communication unit 16 of the diagnosis device 10, and the same description will be omitted.

The storage unit 22 may store data required for recommending cosmetics. Specifically, the storage unit 22 may store information on a diagnosis result of the skin condition and the customized cosmetics. For example, the storage unit 22 may store a table mapping the diagnosis result of the skin condition and ingredients, content, and a mixing ratio of a cosmetic material.

The customized cosmetics DB 24 may be a database in which the diagnosis result of the skin condition and the customized cosmetics information corresponding thereto are accumulated. The customized cosmetics DB 24 may store the diagnosis result of the skin condition and customized cosmetics corresponding thereto whenever receiving the diagnosis result of the skin condition to manage the customized cosmetics information.

The makeup DB 25 may be a database accumulating a makeup image and a cosmetics type or a makeup score used in a makeup image corresponding thereto. It is possible to recommend makeup methods using customized cosmetics recommended to the user via the makeup DB 25.

The operation of each component described above is illustrative, and each component may perform various operations required for recommendation of customized cosmetics.

According to one embodiment of the present invention, the skin management server 20 may include a web application server (WAS). In this case, the skin management server 20 may control transmission and reception of signals within a customized cosmetics provision system. For example, customer identification information, skin diagnosis result information, and information on customized cosmetics may be transmitted and received through the skin management server 20.

In addition, since the WAS may support operation of applications, the skin management server 20 may recommend the customized cosmetics. That is, the skin management server 20 may recommend the customized cosmetics based on the diagnosis result of the skin condition received from the diagnosis device 10, and may transmit information on the customized cosmetics to the manufacturing apparatus 30.

According to another embodiment, the diagnosis device 10 may diagnose a skin condition, and use data stored in the storage unit 17 to recommend customized cosmetics. The diagnosis device 10 may transmit information on the customized cosmetics to the manufacturing apparatus 30.

Thus, the step of recommending cosmetics (S2) may be performed in the diagnosis device 10 or the skin management server 20, but it is illustrative, and a step of recommending cosmetics may be performed in another device except the diagnosis device 10 and the skin management server 20.

Hereinafter, various methods for recommending cosmetics will be described as an example of the diagnosis device 10 performing the step of recommending the cosmetics (S2), but it is not limited thereto. That is, the step of recommending the cosmetics (S2) may be performed by the skin management server 20 or may be performed by the diagnosis device 10 and the skin management server 20 together. However, for convenience of description, a case in which the recommendation is performed by the diagnosis device 10 will be described as an example.

The diagnosis device 10 according to the present invention may recommend the customized cosmetics appropriate for the user based on the diagnosis result of the skin condition. Specifically, the diagnosis device 10 may recommend cosmetic colors, cosmetic ingredients, and the like appropriate for the user's skin color according to the skin condition of the user.

In the present invention, the customized cosmetics may include cosmetics manufactured by mixing cosmetic materials at a predetermined mixing ratio, and commercial cosmetics manufactured already.

A method of recommending cosmetics according to a first embodiment of the present invention uses a database of mixing ratios of cosmetic materials, and is as follows.

The storage unit 17 of the diagnosis device 10 may store a cosmetics manufacturing database including mixing ratios of cosmetic materials.

Here, the mixing ratio of the cosmetic materials may include ingredients of the cosmetic materials, the mixing ratio of each of ingredients, and the ingredients of the cosmetic materials and each ingredient content.

In addition, the mixing ratios of the cosmetic materials may include a mixing ratio for determining a cosmetic color, feeling of cosmetics (for example, moisture or matte, etc.), a mixing ratio for determining coverage, a mixing ratio for determining efficacy (e.g., whitening, pore reduction, wrinkle improvement, etc.), and the like, and may include a mixing ratio considering at least two or more of color, feeling, coverage, and efficacy.

The control unit 19 of the diagnosis device 10 may obtain at least one or more mixing ratios in a cosmetics manufacturing database stored in the storage unit 17 based on a diagnostic result of a skin condition.

In the present invention, the diagnosis result of the skin condition may be information obtained by analyzing the skin condition diagnosed in the step of diagnosing skin (S1). Specifically, the diagnosis result of the skin condition may include skin type, skin tone, skin color, moisture content in skin, sebum content in skin, elasticity of skin, water balance, size and number of wrinkles of skin, size and amount of pores in skin, sensitivity, degree of ultraviolet exposure, sebum secretion, symmetry, cleansing and color makeup, skin age, keratin, skin texture, skin type, skin stress due to exposure to harmful environment and cosmetics use habits, and the like.

The diagnosis result of the skin condition may be an objective diagnosis result or a relative diagnosis result considering the age of the user.

Next, a method of obtaining at least one mixing ratio based on the diagnosis result of the skin condition through an example of the cosmetics manufacturing database shown in FIG. 5 will be described.

Figure 5:
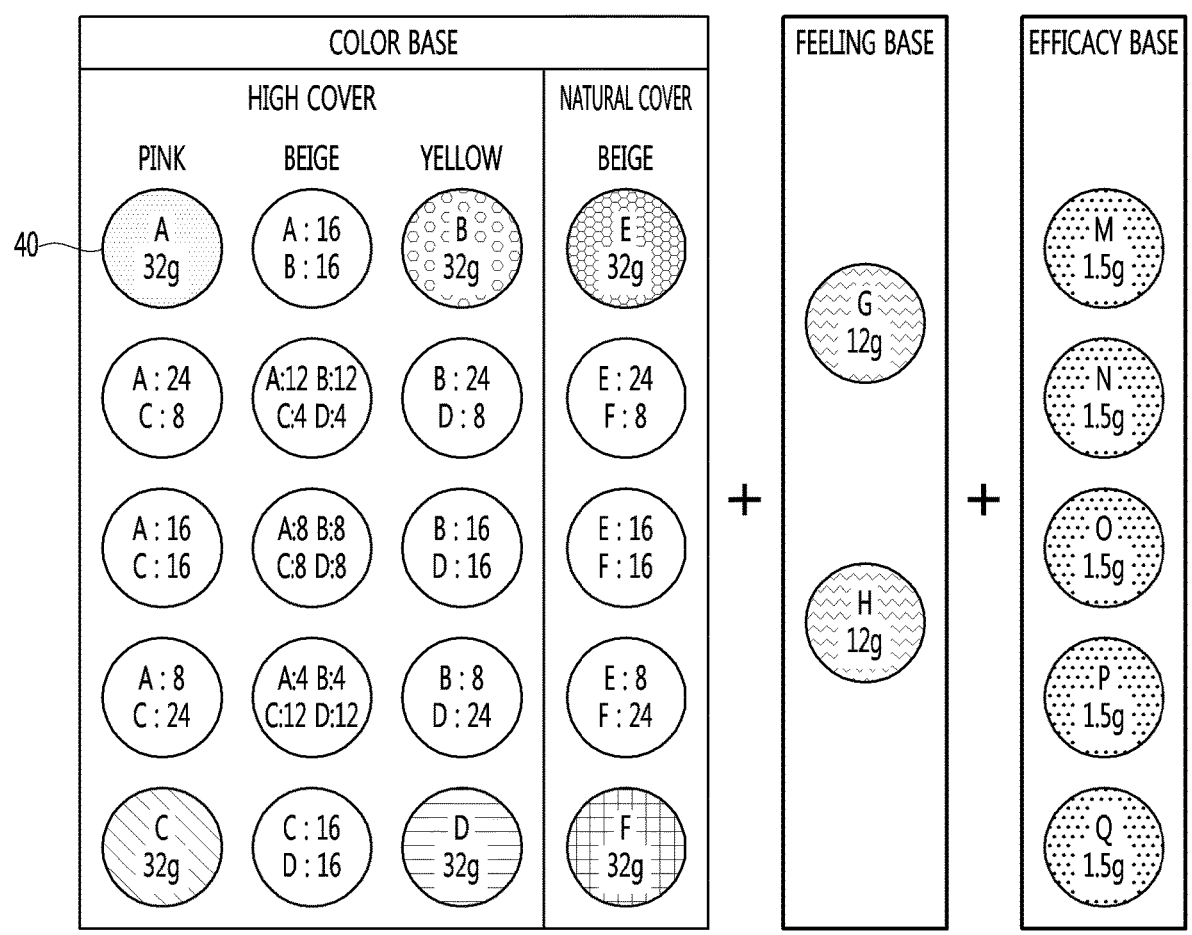
FIG. 5 is an illustrative view illustrating a cosmetics manufacturing database according to one embodiment of the present invention.

FIG. 5 is an exemplary view illustrating a cosmetics manufacturing database according to one embodiment of the present invention.

As shown in FIG. 5, the cosmetics manufacturing database according to an embodiment of the present invention may include a mixing ratio of combining at least one of cosmetic materials A, B, C, D, E, and F, any one of cosmetic materials G and H, and any one of cosmetic materials M, N, O, P, and Q.

In this case, the cosmetic materials A, B, C, D, E and F are materials determining color and coverage of cosmetics. A is a material of bright pink color with high coverage, B is a material of bright yellow color with high coverage, C is a material of dark pink color with high coverage, D is a material of dark yellow color with high coverage, E is a material of light beige color with low coverage, and F is a material of dark beige color with low coverage. However, it is merely illustrative.

The control unit 19 may select any one of the cosmetic materials A, B, C, D, E, and F, or may select a mixing ratio combining two or more cosmetic materials in consideration of skin color, degree of pigmentation, pores, and the like of the user. For example, referring to FIG. 5, any one of a plurality of mixing ratio items 40 included in the cosmetics manufacturing database may be selected.

The mixing ratio item 40 may include the ingredients and amount uses (g) of the cosmetic materials to be used in manufacturing the cosmetics. For example, the mixing ratio item 40 including 'A:24, C:8' may refer to customized cosmetics manufactured by combining 24 g of the cosmetic material A and 8 g of the cosmetic material C.

Meanwhile, the cosmetic materials G and H are materials determining feeling of the cosmetics, and G may be a high moisture material, and H may be a matte material, but it is merely illustrative.

The control unit 19 may select any one of G and H in consideration of water content and sebum content of a user's skin, or may control a mixing ratio of G and H.

In addition, the cosmetic materials M, N, O, P, and Q may be materials determining the efficacy of cosmetics, M may be a wrinkle improving material, N may be a whitening material, O may be a pore reducing material, P may be a sebum controlling material, and Q may be an acne improving material, but it is merely illustrative.

The control unit 19 may select any one of the cosmetic materials M, N, O, P, and Q, or may select a mixing ratio combining at least two thereof based on the diagnosis result of a user's skin condition. For example, the control unit 19 may select the wrinkle improving material M when the number of wrinkles is large in the skin of which the user's skin condition is diagnosed.

Thus, the control unit 19 may set a ratio of the cosmetic material determining the color, the cosmetic material determining the feeling of use, and the cosmetic material determining the efficacy to be different according to the skin condition of the user, and it is possible to recommend appropriate cosmetics.

In addition, in this case, the control unit 19 may determine the ratio of the cosmetic material for determining the color, the cosmetic material for determining the feeling of use, and the cosmetic material for determining the efficacy to be different. For example, the control unit 19 may control the ratio of the cosmetic material determining the color, the cosmetic material determining the feeling of use, and the cosmetic material determining the efficacy to be different such as 6:3:1 or 3:3:3 according to the skin condition of the user.

When using the cosmetics manufacturing database as shown in FIG. 5, there is an advantage that customized cosmetics may be provided to a user with only a small number of cosmetic materials. That is, there is an advantage that various kinds of customized cosmetics may be manufactured by combining limited materials through a cartridge.

Thus, the control unit 19 of the diagnosis device 10 may obtain at least one mixing ratio of cosmetic materials in the cosmetics manufacturing database based on the diagnosis result of the skin condition to recommend customized cosmetics.

Accordingly, since the storage unit 17 stores only one mixing ratio of cosmetic materials, there is an advantage that a space of the storage unit 17 may be saved.

Meanwhile, according to still another embodiment, the storage unit 17 of the diagnosis device 10 may store a database mapping cosmetics types according to the skin condition.

Here, the cosmetics type may be represented to "A type", "B type", etc., and the mixing ratio of the cosmetic materials according to each cosmetics type may be stored in the manufacturing apparatus 30.

Therefore, the diagnosis device 10 may recommend the cosmetics type based on the skin condition of the user and transmit it to the manufacturing apparatus 30, and the manufacturing apparatus 30 may manufacture customized cosmetics according to the mixing ratio of the cosmetic materials corresponding to the received cosmetics type.

Accordingly, since the diagnosis device 10 may store the mixing ratio of the cosmetic materials, there is an advantage that the storage space may be efficiently managed.

A method for recommending cosmetics according to a second embodiment of the present invention is a method for calculating a formula of a cosmetic material, and is as follows.

According to one embodiment, the control unit 19 of the diagnosis device 10 may set each cosmetic material to each axis. The control unit 19 may place a diagnosis result of a user's skin condition in a space corresponding to a cosmetic material on each axis. The control unit 19 may recognize information of coordinates at which the diagnosis result of the skin condition is placed as a mass ratio of a plurality of cosmetic materials. For example, in the control unit 19, when the diagnosis result of the user's skin condition is placed at the coordinates (40, 60) of the space in which the X axis represents a cosmetic material A and the Y axis represents a cosmetic material B, it is possible to recommend cosmetics in which the cosmetic material A and cosmetic material B are mixed in a ratio of 4:6.

According to another embodiment, the control unit 19 of the diagnosis device 10 may obtain L representing brightness, a representing a closer color of red and green, and b representing a closer color of yellow and blue. The control unit 19 may recommend the color of cosmetics by applying the obtained L, a, b to a previously stored formula.

A method of recommending cosmetics according to a third embodiment of the present invention is a method of recommending a makeup color, and is as follows.

The diagnosis device 10 may obtain skin color of a user through the skin diagnosis step (S1). The control unit 19 of the diagnosis device 10 may recommend a makeup color corresponding to the skin color of the user and a cosmetic material corresponding thereto.

According to one embodiment, the storage unit 17 of the diagnosis device 10 stores a makeup color table mapping a skin color and a makeup color so that the control unit 19 may obtain the makeup color according to the skin color of the user.

According to another embodiment, the storage unit 17 of the diagnosis device 10 may store a colorimeter which quantifies skin color based on three indexes of brightness, color and saturation, a numerical value according to the colorimeter, and the relational formula representing the most appropriate makeup color for the skin color. Accordingly, the control unit 19 may obtain a makeup color appropriate for the user through the skin color of the user and the measured colorimeter.

According to still another embodiment, the control unit 19 of the diagnosis device 10 may obtain a skin image of a user, and may perform various image processings on the skin image of the user. Here, the image processing may include complementary color processing, recommended skin color processing, surface color variation processing based on reflectance of skin, and the like. Thus, the control unit 19 may perform various image processings on the skin image to obtain a makeup simulation image. The control unit 19 may recommend an appropriate makeup color to the user based on the simulation image. For example, when the control unit 19 provides a plurality of simulation images to the user through the diagnosis device 10, and receives an input signal for selecting any one of the simulation images from the user, it is possible to obtain a makeup color corresponding to the selected simulation image.

The control unit 19 may recommend customized cosmetics according to the makeup color obtained by various embodiments.

A method for recommending cosmetics according to a fourth embodiment of the present invention is a method of recommending cosmetics in consideration of an inquiry result, and is as follows.

The diagnosis device 10 may receive a signal for inputting a cosmetics type desired by the user through an inquiry method. Specifically, the display unit 18 of the diagnosis device 10 may display at least one question for recommending a cosmetics type to a user. For example, the display unit 18 may display a question of selecting preferred cosmetics from natural cosmetics or high-coverage cosmetics. The user may select the cosmetics to be used through the input unit 11 of the diagnosis device 10.

The diagnosis device 10 may recommend a mixing ratio of at least one cosmetic material in consideration of the user's skin diagnosis result and the inquiry result, respectively or together.

A method for recommending cosmetics according to a fifth embodiment of the present invention is a method for recommending cosmetics in consideration of surrounding elements, and is as follows.

The control unit 19 of the diagnosis device 10 may obtain an age group of a user, skin tone of the user, facial structure of the user, a cosmetic material in use by the user, a favorite fragrance of the user, presence or absence of pigmentation on the user's skin, and the like in the step of diagnosing skin (S1). The control unit 19 may recommend appropriate cosmetics to the user based on the obtained skin tone, facial structure, cosmetic materials in use, skin conditions such as pigmentation, and the like.

For example, when the facial structure of the user is square, it is possible to recommend shading products. For another example, when there are a lot of oil in the cosmetic material in use by the user and a lot of sebum in the user's skin, it is possible to recommend cosmetics with less oil.

According to another embodiment, the control unit 19 of the diagnosis device 10 may obtain at least one of hair color, hair style, face color, and eye color of a user. The control unit 19 may recommend customized cosmetics appropriate for the user in consideration of all the obtained hair color, facial color, and eye color.

Alternatively, the diagnosis device 10 may recommend customized cosmetics based on data mapping the coverage of a makeup product by a degree of pigmentation. Specifically, the degree of pigmentation may refer to an area of the pigment relative to an area of the face, and the coverage of the makeup product may be a product with low coverage, a product with medium coverage, or a product with high coverage, but this classification is merely illustrative. The makeup DB 25 may store data mapping the makeup product coverage by the degree of pigmentation. The diagnosis device 10 may analyze information of the user's pigmentation, and may recommend a makeup product having a coverage appropriate for the user through the makeup DB 25.

Each of the embodiments described above is illustrative, and the diagnosis device 10 may also recommend cosmetics through another method except the cosmetics recommendation method described above.

In addition, each of the embodiments of the cosmetics recommendation method described above may be performed independently, or a plurality of embodiments may be combed. For example, the control unit 19 of the diagnosis device 10 may consider a mixing ratio of cosmetic materials obtained through the cosmetics manufacturing database and favorite cosmetics of the user according to the inquiry result, and may recommend cosmetics manufactured by the mixing ratio of cosmetic materials stored in the cosmetics manufacturing database or a mixing ratio of cosmetic materials not stored in the cosmetics manufacturing database.

The diagnosis device 10 may recommend customized cosmetics based on the diagnosis result of the skin condition, and may transmit information of the recommended customized cosmetics to the manufacturing apparatus 30. The manufacturing apparatus 30 may be controlled so as to provide the customized cosmetics to the user when the customized cosmetics information is received.

At this time, a customized cosmetics provision system according to an embodiment of the present invention may include at least one of a step of obtaining customer information (S4), a step of confirming intention of purchasing customized cosmetics (S5), a step of modifying customized cosmetics (S6), a step of constructing big data of customized cosmetics (S7), and a step of recommending makeup (S8) between the step of recommending customized cosmetics (S2) and the step of providing customized cosmetics (S3).

Hereinafter, each step will be described in detail.

First, the step of obtaining customer information (S4) will be described.

The diagnosis device 10 may receive identification information of a customer.

The identification information of the customer may include at least one of the customer's name, sex, date of birth, contact information, ID, and password.

When the identification information of the customer is input, the diagnosis device 10 may determine whether there is customer information corresponding to the input identification information among the previously stored customer information.

In various embodiments of the present invention, the diagnosis device 10 may store in advance at least one piece of customer information corresponding to at least one piece of identification information, respectively (or including identification information).

The diagnosis device 10 may search whether there is customer information corresponding to the input identification information (or including the input identification information) among at least one piece of customer information previously stored.

When the customer information corresponding to the identification information exists, the diagnosis device 10 may obtain the determined customer information.

In various embodiments, when a customer information management apparatus (not shown) of customized cosmetics is operated separately, the diagnosis device 10 may transmit the identification information input to the customer information management apparatus, and may receive customer information corresponding to the identification information from the customer information management apparatus. The customer information management apparatus may be provided adjacent to the diagnosis device 10 in the same store or at a remote place.

When the customer information corresponding to the identification information does not exist, the diagnosis device 10 may receive customer information.

The diagnosis device 10 may display a user interface (UI, GUI) for receiving customer information, and may obtain customer information inputted through the displayed user interface. The customer information obtained by the diagnosis device 10 may include the identification information inputted above.

In one embodiment, the diagnosis device 10 may display a user interface for inquiring whether to input customer information to a customer, and may receive customer information corresponding to a response of the customer inputted through the user interface. For example, the diagnosis device 10 may display a user interface for receiving customer information when an affirmative response is input through the user interface for inquiring whether to input customer information.

In one embodiment, the diagnosis device 10 may display a user interface for inquiring whether or not to consent to the collection and utilization of personal information to the customer, and may receive the customer information in response to the customer's response input through the user interface. For example, the diagnosis device 10 may display a user interface for receiving customer information when a consent response is input through the user interface for inquiring whether or not to consent to the collection and utilization of personal information.

In the above description, the customer information is obtained in response to the input of the identification information, but the present invention is not limited thereto. As an example, in various embodiments, when the diagnosis device 10 does not store and manage identification information of a customer and customer information corresponding thereto, or when the customer information management apparatus does not exist separately, the diagnosis device 10 may omit the operation of confirming the previously stored customer information corresponding to the identification information, and may obtain the customer information by displaying the user interface for immediately receiving the customer information input.

In addition, the diagnosis device 10 may display the obtained customer information so that the customer may confirm it, or store and manage the obtained customer information in a customized cosmetics database for each customer. In one embodiment, when the customer information management apparatus is provided separately, the diagnosis device 10 may transmit the obtained customer information to the customer information management apparatus.

In various embodiments of the present invention, the diagnosis device 10 may create and manage a customized cosmetics database for each customer by storing a result of skin diagnosis and customized cosmetics recommendation performed after customer information is obtained in response to customer information.

Next, the step of confirming intention of purchasing the customized cosmetics (S5) according to the present invention will be described.

The step of confirming intention of purchasing the customized cosmetics (S5) may be a step of displaying the customized cosmetics recommended to the user through the diagnosis result of the skin condition and confirming the purchase intention of the customized cosmetics displayed to the user.

Figure 6:
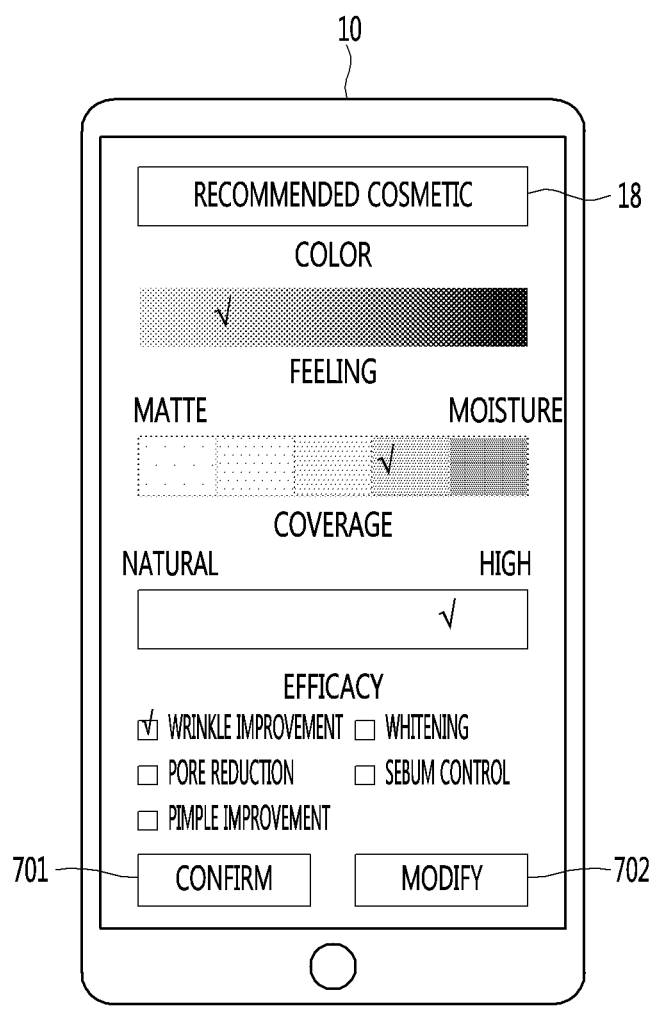
FIG. 6 is an illustrative view of a screen displayed at a step of confirming intention of purchasing customized cosmetics according to an embodiment of the present invention.

FIG. 6 is an illustrative view of a screen displayed at a step of confirming intention of purchasing customized cosmetics according to an embodiment of the present invention.

According to one embodiment, the skin management server 20 may receive a diagnosis result of a skin condition from the diagnosis device 10 to recommend customized cosmetics. In this case, the communication unit 21 of the skin management server 20 may transmit recommended customized cosmetics information to the diagnosis device 10. The diagnosis device 10 may receive the customized cosmetics information from the skin management server 20, and the display unit 18 may display the received customized cosmetics information.

According to another embodiment, the diagnosis device 10 may recommend customized cosmetics based on the diagnosis result of the skin condition, and may display information on the customized cosmetics on the display unit 18.

As shown in FIG. 6, the display unit 18 of the diagnosis device 10 may display information of the customized cosmetics. The information of the customized cosmetics may include cosmetic color information, feeling information, coverage information, and efficacy information. A method of displaying the information of the customized cosmetics shown in FIG. 6 is illustrative, and is not limited thereto.

The input unit 11 of the diagnosis device 10 may receive an instruction selecting a confirm icon 701 or a modify icon 702 while displaying information of the customized cosmetics.

When the input unit 11 of the diagnosis device 10 receives an instruction selecting the confirm icon 701, the communication unit 16 may transmit the displayed customized cosmetics information to the manufacturing apparatus 30. On the other hand, when the input unit 11 of the diagnosis device 10 receives an instruction selecting the modify icon 702, the display unit 18 may display a modification screen of the customized cosmetics.

Next, the step of modifying the customized cosmetics (S6) according to the present invention will be described.

The step of modifying the customized cosmetics (S6) may refer to a step of modifying some or all of the recommended customized cosmetics through user input.

When receiving an instruction selecting the modify icon 702 shown in FIG. 6, the display unit 18 of the diagnosis device 10 may display a customized cosmetics modification screen for modifying the customized cosmetics.

Figure 7:
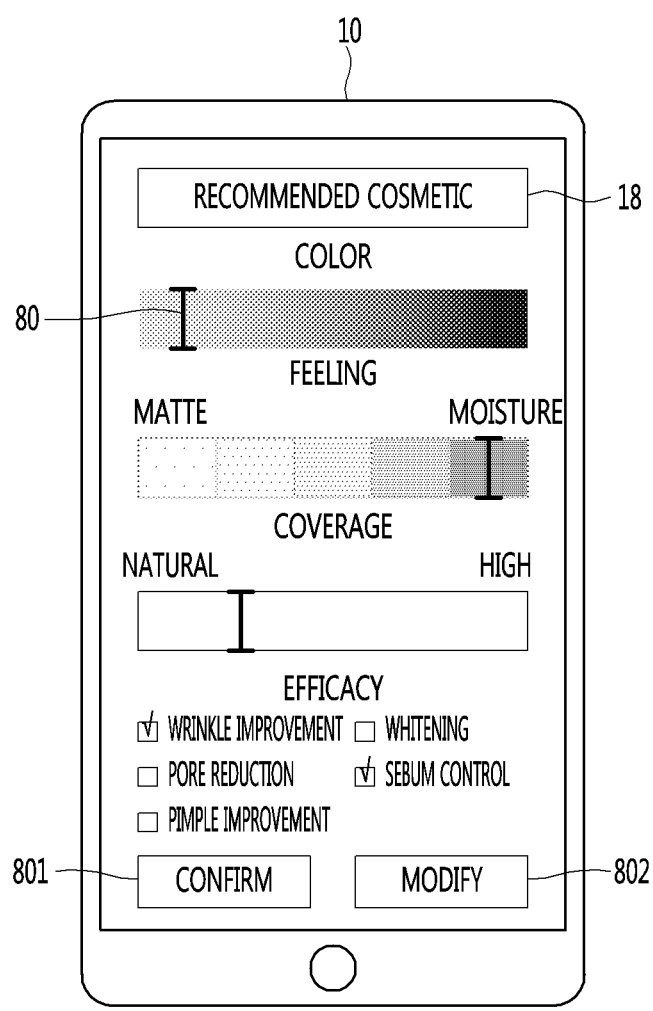
FIG. 7 is an illustrative view of a screen of modifying customized cosmetics according to an embodiment of the present invention.

FIG. 7 is an illustrative view of a screen of modifying customized cosmetics according to an embodiment of the present invention.

As shown in FIG. 7, a customized cosmetics modification screen may include a modification bar 70 for changing information of customized cosmetics, together with the information of customized cosmetics. The user may receive an instruction moving a location of the modification bar 70 through the input unit 11. The display unit 18 may change and display the location of the modification bar 70 according to the instruction moving the location of the modification bar 70.

The customized cosmetics modification screen may further include a confirm icon 801 and a cancel icon 802 to cancel the modification of the customized cosmetics.

When receiving the instruction selecting the confirm icon 801, the input unit 11 of the diagnosis device 10 transmits the modified customized cosmetics information to the manufacturing apparatus 30, and when receiving the instruction selecting the cancel icon 802, the input unit 11 deletes the changed information and may display again the screen as shown in FIG. 6.

Next, the step of constructing big data of the customized cosmetics (S7) according to the present invention will be described.

The skin management server 20 may include the customized cosmetics database (DB) that accumulates data of a customized cosmetics provision system.

The customized cosmetics DB 24 according to the present invention may store the diagnosis result of the skin condition, the customized cosmetics information based on the diagnosis result of the skin condition, and at least one piece of customized cosmetics data mapping the modified information when there is a modification of the customized cosmetics.

When new customized cosmetics data is received, the control unit 23 of the skin management server 20 may add it to the customized cosmetics DB 24. That is, the skin management server 20 may perform a management such as collecting customized cosmetics data in the customized cosmetics DB 24, and storing and updating the customized cosmetics data.

The control unit 23 of the skin management server 20 may recommend the appropriate cosmetics for the user in consideration of the data stored in the storage unit 22 and the data stored in the customized cosmetics DB 24.

Therefore, after recommending the customized cosmetics, the control unit 23 of the skin management server 20 may confirm to the user via the diagnosis device 10 whether to add the customized cosmetics data to the customized cosmetics DB 24.

Figure 8:
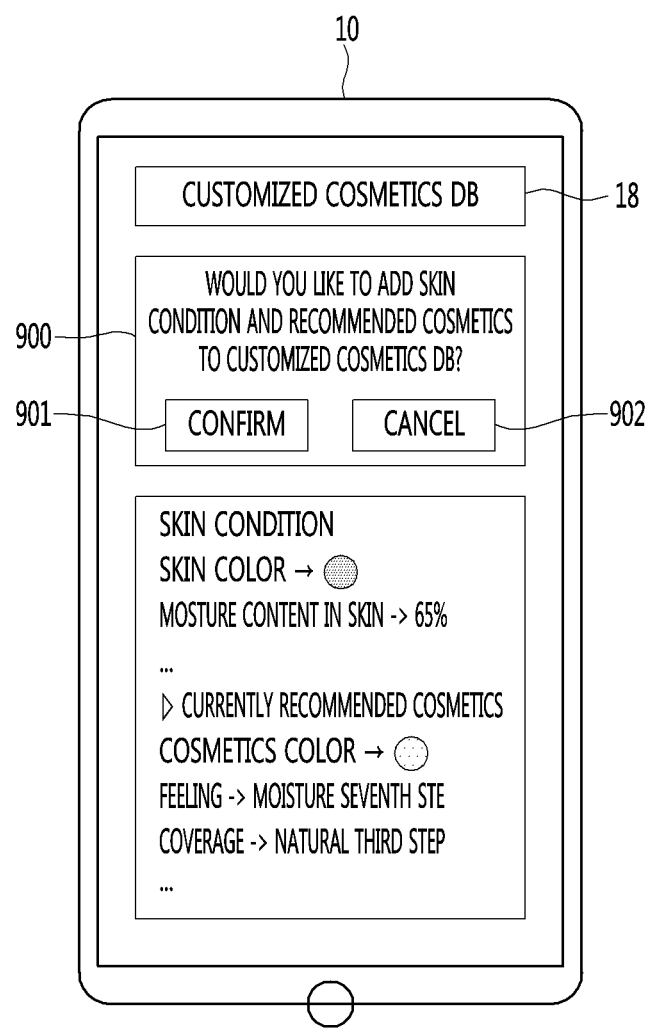
FIG. 8 is an illustrative screen displayed at a step of constructing big data of customized cosmetics according to an embodiment of the present invention.

FIG. 8 is an illustrative screen displayed at a step of constructing big data of customized cosmetics according to an embodiment of the present invention.

As shown in FIG. 8, the display unit 18 of the diagnosis device 10 may display a window 900 for confirming whether to store customized cosmetics data including a skin condition and customized cosmetics information. At this time, the display unit 18 may further display the skin condition and the customized cosmetics information to be stored.

A user may confirm the skin condition and the customized cosmetics information, and may determine whether the customized cosmetics data is stored in the customized cosmetics DB 24.

When receiving an instruction selecting a storage icon 901, the input unit 11 of the diagnosis device 10 may store the customized cosmetics data mapping the skin condition and the customized cosmetics information in the customized cosmetics DB 24. On the other hand, when receiving an instruction selecting a cancel icon 902, the input unit 11 may delete the skin condition and the customized cosmetics information.

However, a screen displaying whether or not to store the customized cosmetics data shown in FIG. 8 is merely illustrative, and is not limited thereto.

According to another embodiment, the display unit 18 of the diagnosis device 10 may display a window (not shown) confirming whether or not to consent to the utilization of personal information at the time of using a service of providing customized cosmetics. The input unit 11 of the diagnosis device 10 may receive an instruction selecting consent of personal information or an instruction for non-consent of personal information (instruction not to select consent of personal information). The control unit 19 of the diagnosis device 10 may store customized cosmetics data mapping a skin condition and customized cosmetics information in the customized cosmetics DB 24 when the instruction selecting consent of personal information is received. That is, when receiving the instruction selecting consent of personal information, the control unit 19 of the diagnosis device 10 may store the customized cosmetics data in which the skin condition and the customized cosmetics information are mapped in the customized cosmetics DB 24, without displaying a screen as shown in FIG. 8. In this case, there is an advantage that it is not necessary to display the screen as shown in FIG. 8 every time when the customized cosmetics are recommended through one-time consent of personal information.

Thus, when the customized cosmetics provision system according to the present invention includes the step of constructing big data of the customized cosmetics (S7), there is an advantage that it is possible to recommend more appropriate cosmetics to a user's skin condition by using accumulated data, to easily grasp trends in cosmetics and user preferences, and the like.

Next, the step of recommending makeup (S8) according to the present invention will be described.

The skin management server 20 may include a makeup database (DB) including a makeup image and a cosmetics type used in the makeup image.

The makeup DB 25 according to the present invention may store a makeup image and at least one piece of makeup data mapping the cosmetics type used in the makeup image. The makeup data may further include the makeup image, a skin condition, a makeup score, and the like in addition to the cosmetics type used in the makeup image.

The control unit 23 of the skin management server 20 may extract any one of the makeup images stored in the makeup DB 25 based on the diagnosis result or the customized cosmetics of the skin condition to recommend it to the user.

Figure 9:
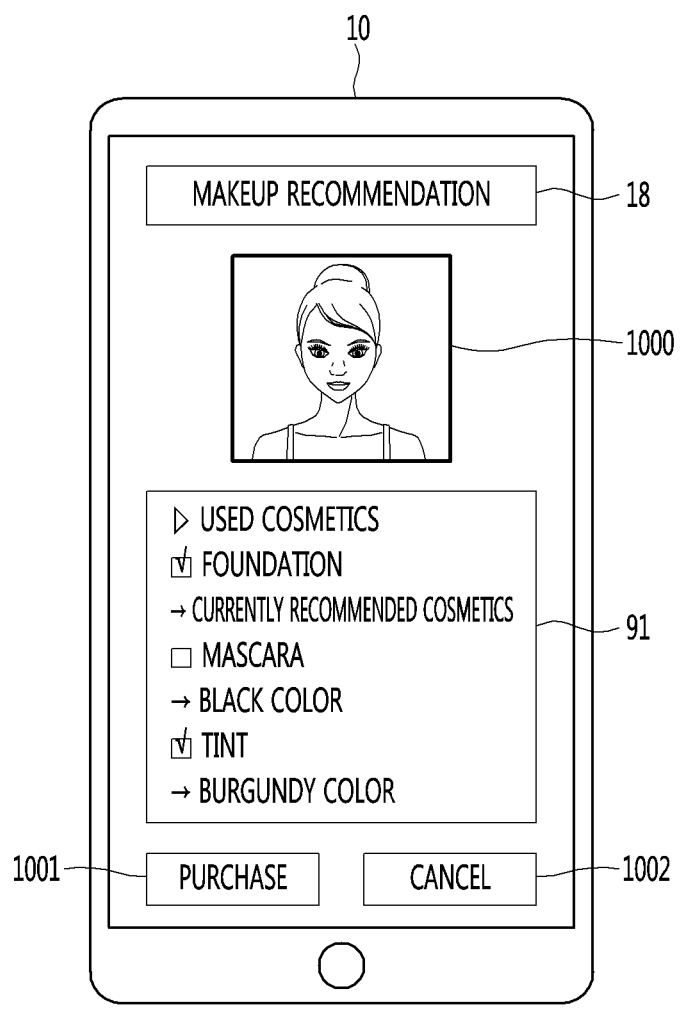
FIG. 9 is an illustrative view of a screen displayed at a step of recommending makeup according to an embodiment of the present invention.

FIG. 9 is an illustrative view of a screen displayed at a step of recommending makeup according to an embodiment of the present invention.

The control unit 23 of the skin management server 20 may extract any one makeup image from the makeup DB 25 based on at least one of a diagnosis result and customized cosmetics of a skin condition. For example, the control unit 23 may extract the makeup image in which the customized cosmetics is used. The communication unit 21 of the skin management server 20 may transmit the extracted makeup image to the diagnosis device 10.

The diagnosis device 10 may display a makeup image 1000 received from the skin management server 20 and a makeup recommendation screen including cosmetics 91 used in the makeup image. The cosmetics used in the makeup image 1000 may include or may not include the cosmetics recommended in the step of recommending customized cosmetics (S2).

The input unit 11 of the diagnosis device 10 may receive an instruction selecting a part or all of the cosmetics 91 displayed on the makeup recommendation screen. When receiving an instruction selecting a purchase icon 1001, the input unit 11 of the diagnosis device 10 may transmit information of the selected cosmetics to the manufacturing apparatus 30. When receiving an instruction selecting a cancel icon 1002, the input unit 11 of the diagnosis device 10 may delete the information of the selected cosmetics.

Thus, when the customized cosmetics provision system according to the present invention includes the step of recommending makeup (S8), it is possible to recommend the customized cosmetics to the user. At the same time, since the user may preview the makeup image using the customized cosmetics, there is an advantage that an effect expected when a makeup product is purchased may be previewed.

Next, the step of providing the customized cosmetics (S3) according to an embodiment of the present invention will be described.

The step of providing the customized cosmetics according to the present invention may refer to the step of providing the customized cosmetics recommended by the manufacturing apparatus 30 through the step of recommending customized cosmetics (S2). Here, the provision of customized cosmetics may include the provision of cosmetics manufactured according to a mixing ratio of cosmetic materials and the provision of commercial cosmetics manufactured already.

First, a method of manufacturing the customized cosmetics according to the mixing ratios of cosmetic materials by the manufacturing apparatus 30 will be described.

The diagnosis device 10 or the skin management server 20 may transmit information of customized cosmetics to the manufacturing apparatus 30.

When a communication unit (not shown) of the manufacturing apparatus 30 receives the mixing ratio of the cosmetic materials required for manufacturing the customized cosmetics from the skin management server 20, the manufacturing apparatus 30 may manufacture the cosmetics based on the received mixing ratio of the cosmetic materials.

Hereinafter, a method of manufacturing customized cosmetics according to various embodiments of the present invention will be described.

A method for manufacturing cosmetics according to a first embodiment of the present invention uses a cartridge replacement type cosmetics manufacturing apparatus, and is as follows.

Figure 10:
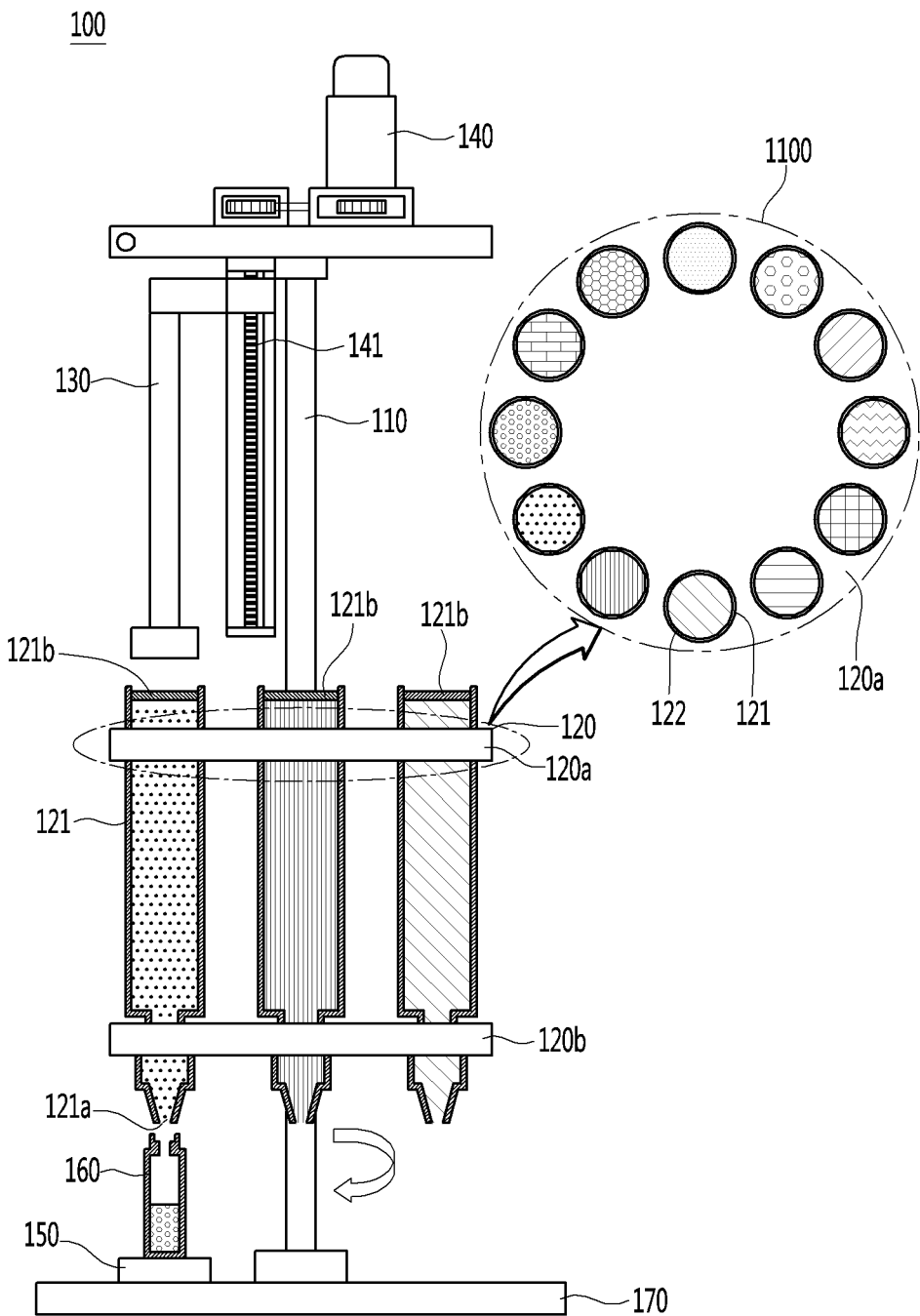
FIGS. 10 and 11 are views for describing a cartridge replacement type cosmetics manufacturing apparatus of according to an embodiment of the present invention.
Figure 11:
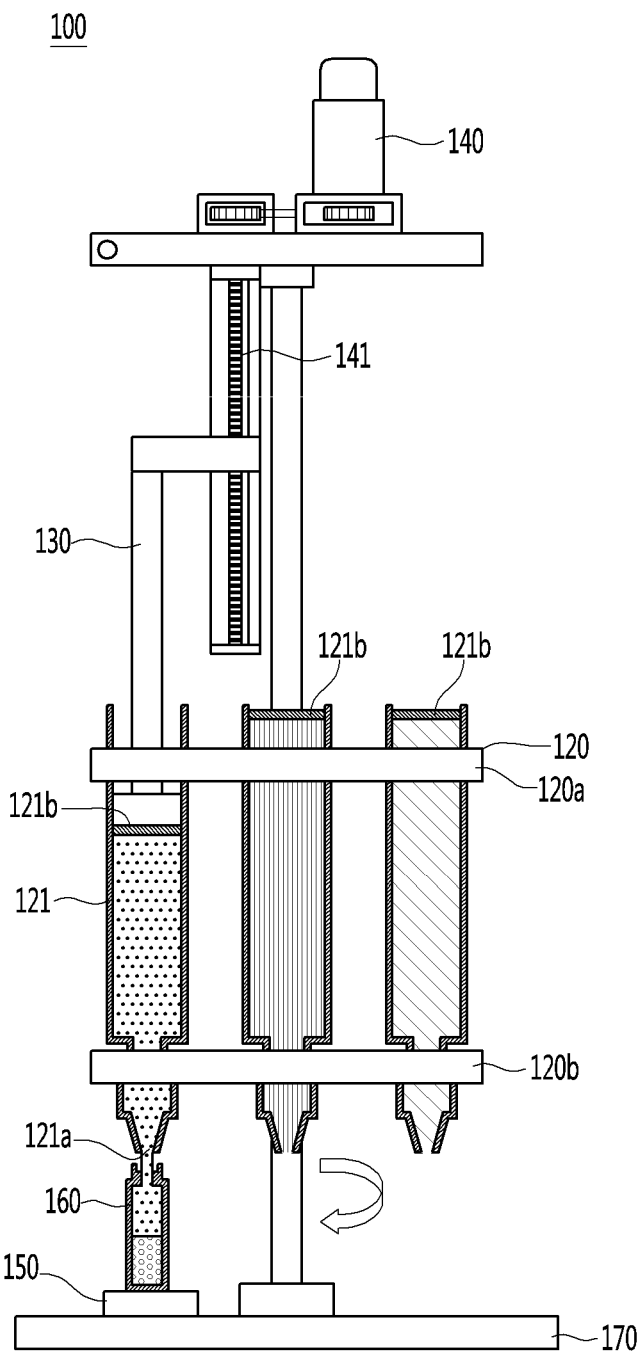

FIGS. 10 and 11 are views for describing a cartridge replacement type cosmetics manufacturing apparatus according to an embodiment of the present invention. Specifically, FIG. 10 is a cross-sectional view illustrating a state in which a compression member 130 of a cartridge replacement type cosmetics manufacturing apparatus 100 is moved up, and FIG. 11 is a cross-sectional view illustrating a state in which the compression member 130 of the cartridge replacement type cosmetics manufacturing apparatus 100 is moved down.

The manufacturing apparatus 30 of the customized cosmetics provision system may include the cartridge replacement type cosmetics manufacturing apparatus 100.

The cartridge replacement type cosmetics manufacturing apparatus 100 according to an embodiment of the present invention may include a main body 110, a cartridge support 120, a cartridge 121, a compression member 130, a motor 140, a sensor 150, a cosmetics container 160, and a main body support 170. However, it is illustrative, and a part of the components listed above may be omitted or another component may be further included.

The main body 110 may be connected to the cartridge support 120 and the motor 140 to mount the cartridge support 120 and the motor 140, respectively.

The cartridge support 120 and the motor 140 may move while the cartridge replacement type cosmetics manufacturing apparatus 100 is operated, and the main body 110 may prevent the cartridge replacement type cosmetics manufacturing apparatus 100 from being shaken by the movement of the cartridge support 120 and the motor 140.

The cartridge support 120 may accommodate a plurality of cartridges 121. A plurality of through holes 122 passing through in the vertical direction and accommodating the cartridges 121, may be formed in the cartridge support 120.

A circular image shown in FIG. 10 shows a state in which the cartridge 121 is inserted into each of the through holes 122 as viewed from the vertical direction.

The cartridge support 120 may be divided into an upper cartridge support 120a and a lower cartridge support 120b, and a through hole 122 formed in the upper cartridge support 120a may be larger than a through hole 122 formed in the lower cartridge support 120b.

The cartridge support 120 may rotate clockwise or counterclockwise.

Alternatively, the main body support 170 supporting the cosmetics container 160 may be rotated clockwise or counterclockwise.

The main body support 170 may further include a sensor 150, and in this case, the sensor 150 and the cosmetics container 160 may rotate together with the main body support 170.

The cartridge 121 may contain a cosmetic material. In particular, the plurality of cartridges 121 may contain different cosmetic materials, respectively. The cartridge 121 may be mounted on the cartridge support 120. The cartridge 121 may be inserted into or separated from the through hole 122 formed in the cartridge support 120. For example, when all of the cosmetic materials contained in the cartridge 121 are consumed, an empty cartridge 121 may be separated from the cartridge support 120, and a new cartridge 121 may be inserted. Alternatively, when all of the cosmetic materials contained in the cartridge 121 are consumed, the cosmetic materials may be refilled into the cartridge 121. The refilling of the cosmetic material is possible both in the state in which the cartridge 121 is mounted on the cartridge support 120 or separated therefrom.

A material injection hole 121a and a cartridge stopper 121b may be formed at the cartridge 121. A cross sectional size in the horizontal direction of the material injection hole 121a may be smaller than a cross sectional size in the horizontal direction of the cartridge stopper 121b.

The cartridge stopper 121b may protect the cosmetic materials contained in the cartridge 121.

The cartridge stopper 121b may be formed with a surface to which the compression member 130 applies pressure. The cartridge stopper 121b may be inserted into the cartridge 121 when the compression member 130 applies pressure to the cartridge stopper 121b. The compression member 130 may compress the cosmetic materials inserted into the cartridge 121 and contained in the cartridge 121, and may discharge them to an outside of the cartridge 121. When the compression member 130 pushes the cosmetic materials downward, the cosmetic materials contained in the cartridge 121 may be injected into the cosmetics container 160 through the material injection hole 121a. Specifically, when the compression member 130 is lowered downward as shown in FIG. 11 after the compression member 130 is positioned upward as shown in FIG. 10, the cosmetic materials contained in the cartridge 121 may be contained in the cosmetics container 160.

As the cartridge support 120 rotates, the cartridge 121 located above the cosmetics container 160 may be changed. Therefore, the cosmetic materials are changed while the cartridge support 120 rotates, and may be injected into the cosmetics container 160.

The compression member 130 may be mounted at the motor 140. The motor 140 may be formed with a rack 141 protruding downward, and the compression member 130 may be engaged with the rack to move up.

The motor 140 may be mounted above the cartridge support 120 to move up the compression member 130. The motor 140 may move down the compression member 130 based on the mixing ratio of the cosmetic materials. Specifically for example, when the mixing ratio of the cosmetic materials is (cosmetic material A):(cosmetic material B)=7:3, a ratio of a descent length of the compression member 130 with respect to the cartridge 121 containing the cosmetic material A and a descent length of the compression member 130 with respect to the cartridge 121 containing the cosmetic material B may be 7:3. That is, the motor 140 may move down the compression member 130 in accordance with the mixing ratio of the cosmetic materials to inject the cosmetic materials into the cosmetics container 160.

The descent distance of the compression member 130 may be set by a control unit (not shown). The control unit (not shown) may control the descent distance of the compression member 130 based on the received mixing ratio of the cosmetic materials.

Alternatively, the descending distance of the compression member 130 may be set by the sensor 150.

The sensor 150 may measure a weight of the cosmetics container 160. For example, the sensor 150 may be an electronic scale of a load cell type.

The sensor 150 may measure the weight of the cosmetics container 160 to measure the weight of the cosmetic materials injected into the cosmetics container 160. The control unit (not shown) may control the moving up of the compression member 130 by using the weight of the cosmetic materials measured through the sensor 150.

Meanwhile, the cartridge 121 may be formed in a form of an airless pump container. When the cartridge 121 is the airless pump container, the cosmetic materials may be injected into the cosmetics container 160 by pumping.

The cosmetics container 160 may contain the cosmetic materials injected from the cartridge 121.

The cosmetics container 160 may contain the cosmetic materials injected according to the mixing ratio of the cosmetic materials, and the cosmetic materials may be mixed.

The cartridge replacement type cosmetics manufacturing apparatus 100 may further include a mixing device (not shown). The mixing device (not shown) may be driven such that the cosmetic materials contained in the cosmetics container 160 is uniformly mixed.

Meanwhile, the cartridge replacement type cosmetics manufacturing apparatus 100 may be formed such that the material injection hole 121a is located in a lateral direction, unlike those shown in FIGS. 10 and 11. That is, the motor 140 moves the compression member 130 in the lateral direction, and the cosmetic materials contained in the cartridge 121 may be discharged in the lateral direction to be contained in the cosmetics container 160.

In this way, when the cartridge replacement type cosmetics manufacturing apparatus 100 according to an embodiment of the present invention is used, there is an advantage that customized cosmetics may be easily manufactured. In addition, since the cartridge 121 is frequently replaced, there is an advantage that contamination possibility may be lowered.

A method of manufacturing cosmetics according to a second embodiment of the present invention uses a nozzle type cosmetics blending apparatus, and is as follows.

The manufacturing apparatus 30 of the customized cosmetics provision system may include a nozzle type cosmetics blending apparatus 200.

Figure 12:
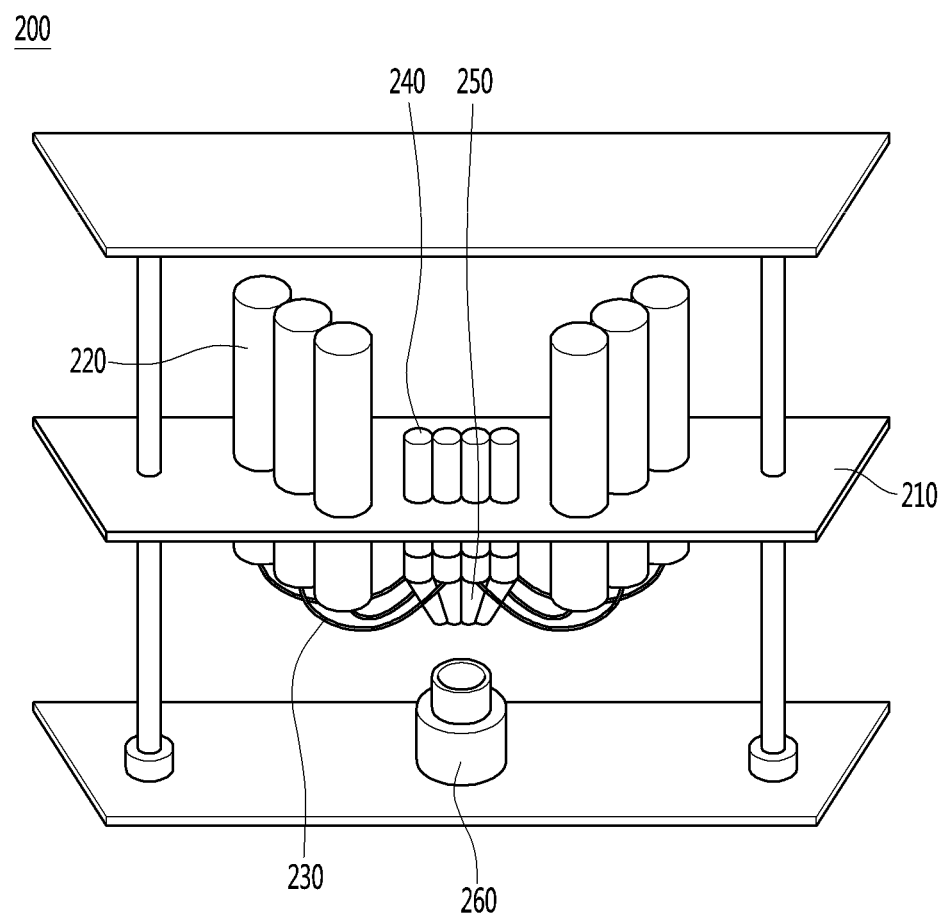
FIG. 12 is a view for describing a nozzle type cosmetics blending apparatus according to an embodiment of the present invention.

FIG. 12 is a view for describing a nozzle type cosmetics blending apparatus according to an embodiment of the present invention.

The nozzle type cosmetics blending apparatus 200 may include a main body 210, a canister 220, a pipe 230, a pump 240, a needle nozzle 250, and a cosmetics container 260. However, it is illustrative, and a part of the components listed above may be omitted or another component may be further included.

The canister 220, the pump 240, and the needle nozzle 250 may be mounted on the main body 210.

The canister 220 may contain cosmetic materials. The nozzle type cosmetics blending apparatus 200 may include a plurality of canisters 220, and each of the plurality of canisters 220 may include different cosmetic materials.

Each of the plurality of canisters 220 may be connected to the pipe 230.

The pipe 230 may connect each of the plurality of canisters 220 with the pump 240. The cosmetic materials contained in the canister 220 may be moved to the pump 240 along the pipe 230.

When the pump 240 operates, an internal pressure is generated, and the cosmetic materials contained in the canister 220 may move in the direction of the pump 240 along the pipe 230 by the internal pressure.

The cosmetic materials moved to the pump 240 may be injected into the cosmetics container 260 by the needle nozzle 250.

Meanwhile, the nozzle type cosmetics blending apparatus 200 may further include a mixing device (not shown). The nozzle type cosmetics blending apparatus 200 may be driven such that the cosmetic materials contained in the cosmetics container 260 are uniformly mixed by the mixing device (not shown).

In this way, when the nozzle type cosmetics blending apparatus 200 according to an embodiment of the present invention is used, there is an advantage that the cosmetics may be manufactured stably because they do not shake by the movement of the nozzle type cosmetics blending apparatus itself.

Each embodiment described above is illustrative, and the manufacturing apparatus 30 may include another apparatus capable of manufacturing cosmetics by mixing various cosmetic materials except the apparatuses described above.

Next, a method for delivering customized cosmetics to a user in the step of providing customized cosmetics (S3).

Figure 13:
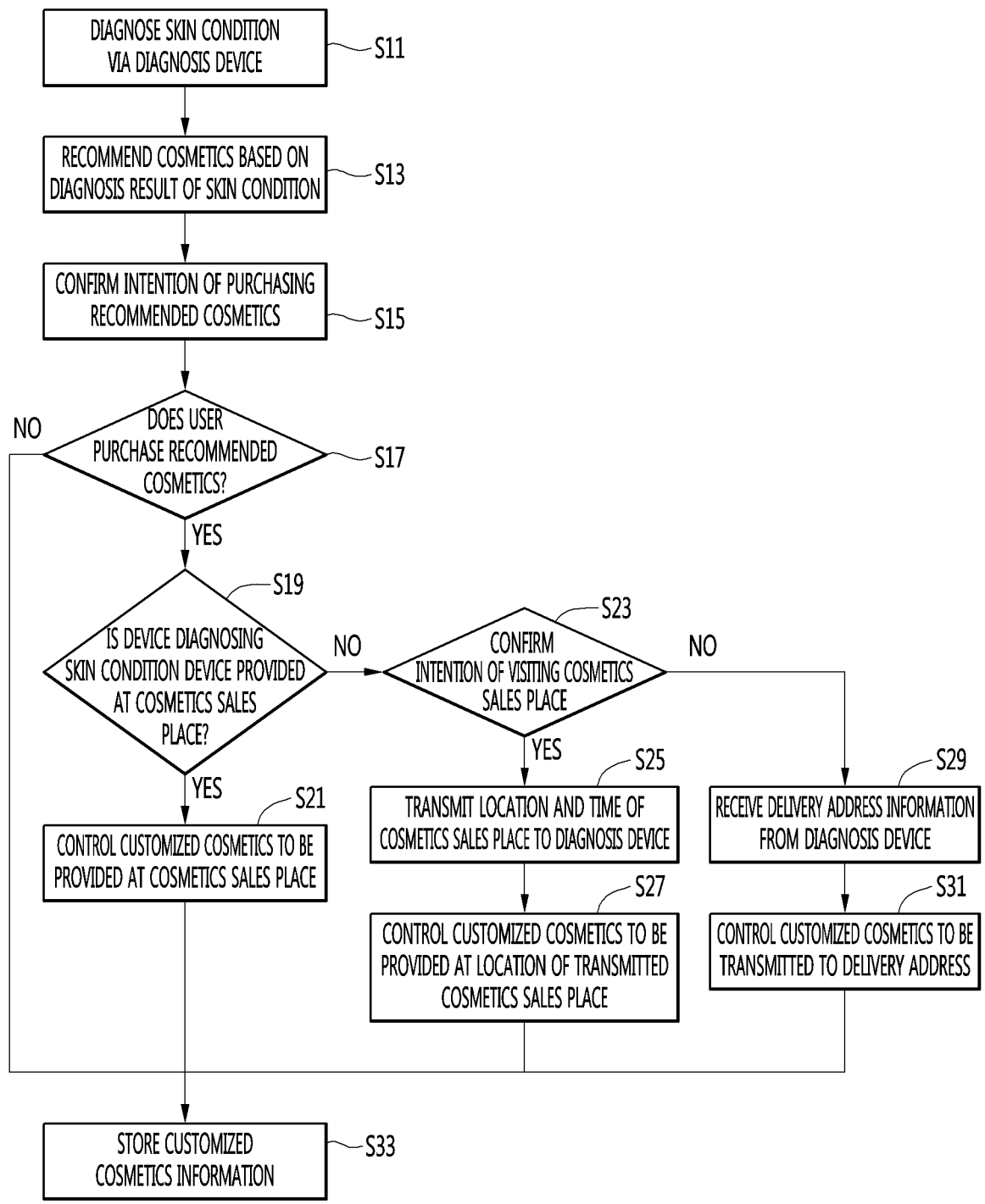
FIG. 13 is a flowchart for describing a method of delivering customized cosmetics in a customized cosmetics provision system according to an embodiment of the present invention.

Next, FIG. 13 is a flowchart for describing a method of delivering customized cosmetics in a customized cosmetics provision system according to an embodiment of the present invention.

The diagnosis device 10 may diagnose a skin condition (S11).

In the present invention, the diagnosis device 10 may be a professional skin diagnosis device which is provided at a cosmetics sales place or a personal mobile terminal.

In the present invention, the cosmetics sales place may include all places where cosmetics may be sold, such as a cosmetics sales store, a dermatologist, an esthetic shop, a door-to-door shop, and an online mall.

The diagnosis device 10 or the skin management server 20 may recommend customized cosmetics based on a diagnosis result of the skin condition (S13).

The diagnosis device 10 or the skin management server 20 may confirm intention of purchasing the customized cosmetics (S15).

The diagnosis device 10 or the skin management server 20 may confirm intention of purchasing the customized cosmetics through a screen as shown in FIG. 6 or FIG. 7 described above, but it is merely illustrative.

The user may input intention of purchasing the customized cosmetics through the diagnosis device 10, and the diagnosis device 10 may transmit a purchase intention input signal of the user to the skin management server 20.

The diagnosis device 10 or the skin management server 20 confirms intention of purchasing the customized cosmetics of the user (S17), and when the user intends to purchase the customized cosmetics, it is possible to determine whether the diagnosis device 10 diagnosing the skin condition is a diagnosis device provided at the cosmetics sales place (S19).

The diagnosis device 10 or the skin management server 20 may control so as to deliver the customized cosmetics at the cosmetics sales place when the diagnosis device diagnosing the skin condition is a diagnosis device provided at the cosmetics sales place (S21).

That is, the diagnosis device 10 or the skin management server 20 may transmit a mixing ratio of cosmetic materials to the manufacturing apparatus 30 provided at the cosmetics sales place when the customized cosmetics are cosmetics manufactured according to the mixing ratio of the cosmetic materials. The manufacturing apparatus 30 may manufacture the cosmetics according to the received mixing ratio of the cosmetic materials. Accordingly, the user may be provided with the customized cosmetics at the cosmetics sales place.

Likewise, when the customized cosmetics are commercial cosmetics that have been produced and sold, the user may be provided the products at the cosmetics sales place.

On the other hand, the diagnosis device 10 or the skin management server 20 may confirm intention of visiting the cosmetics sales place (S23) when the diagnosis device 10 diagnosing the skin condition is not a diagnosis device provided at the cosmetics sales place.

The skin management server 20 may determine intention of visiting the cosmetics sales place through the diagnosis device 10.

When determining that the user intends to visit the cosmetics sales place, the skin management server 20 may transmit the location and the visit time of the cosmetics sales place to the diagnosis device 10 (S25).

Figure 14:
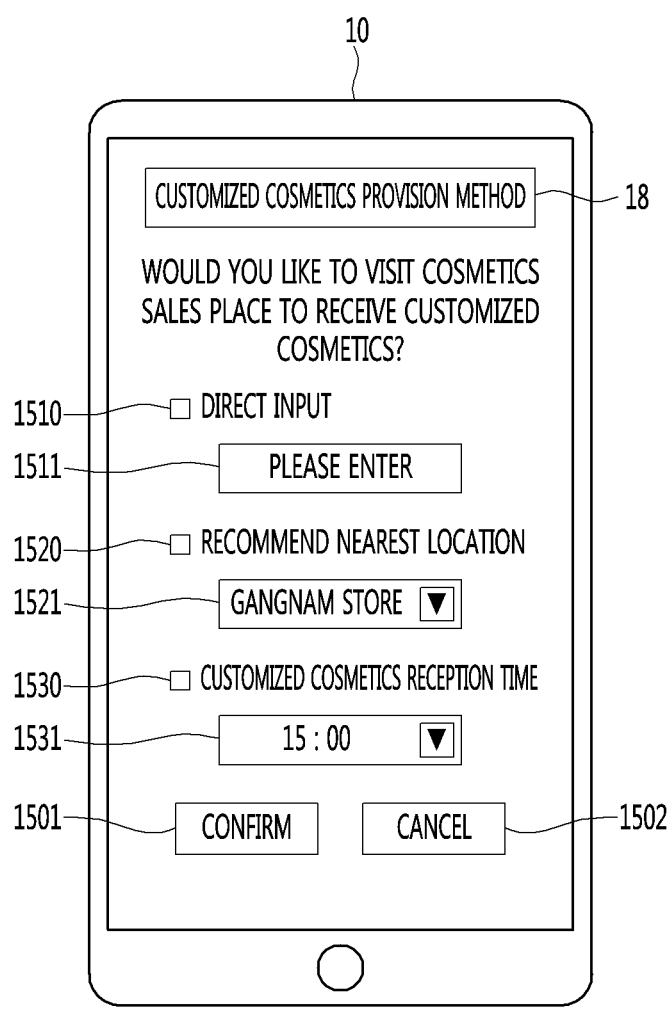
FIG. 14 is an illustrative screen for determining intention of visiting to a cosmetics sales place according to an embodiment of the present invention.

FIG. 14 is an illustrative screen for determining intention of visiting a cosmetics sales place according to an embodiment of the present invention.

The display unit 18 of the diagnosis device 10 may display a screen for selecting a method of delivering customized cosmetics as shown in FIG. 14.

The input unit 11 of the diagnosis device 10 may receive an instruction selecting either one of a direct input item 1510 or a near location recommend item 1520 and a confirm icon 1501.

The user may input a desired cosmetics sales place through the direct input item 1510 to receive cosmetics.

Alternatively, the user may receive the cosmetics at a nearby cosmetics sales place.

In this case, the diagnosis device 10 or the skin management server 20 may control so as to provide the customized cosmetics at a location of the cosmetics sales place closest to a location of the cosmetics sales place received via a user input or to a user's current location based on GPS.

When the nearby cosmetics sales place is recommended, the diagnosis device 10 may further display an icon 1521 for changing the cosmetics sales place together with a location of the recommended cosmetics sales place. When the diagnosis device 10 receives an instruction selecting the icon 1521 for changing the cosmetics sales place, the changed cosmetics sales place is transmitted to the skin management server 20 so that the customized cosmetics may be provided at the changed cosmetics sales place.

In addition, the diagnosis device 10 may receive an instruction selecting a time of receiving the customized cosmetics. As shown in FIG. 14, the diagnosis device 10 may receive an instruction selecting a time of receiving the customized cosmetics by displaying an item 1530 selecting a time of receiving the customized cosmetics.

The skin management server 20 may transmit a location and time of the cosmetics sales place in which the customized cosmetics are provided to the diagnosis device 10. The customized cosmetics may be delivered the user by referring to a visit location and visit time of the cosmetics sales place received at the diagnosis device 10 and visiting the cosmetics sales place in which the customized cosmetics are provided.

The skin management server 20 may control such that the customized cosmetics are provided at the location of the cosmetics sales place transmitted to the diagnosis device 10. The details are similar to those described in S21, and will be omitted.

On the other hand, the input unit 11 of the diagnosis device 10 may receive an instruction selecting a cancel icon 1502 on a screen as shown in FIG. 14.

In this case, the skin management server 20 determines that the user does not intend to visit the cosmetics sales place, and may receive delivery address information from the diagnosis device 10 (S29).

Figure 15:
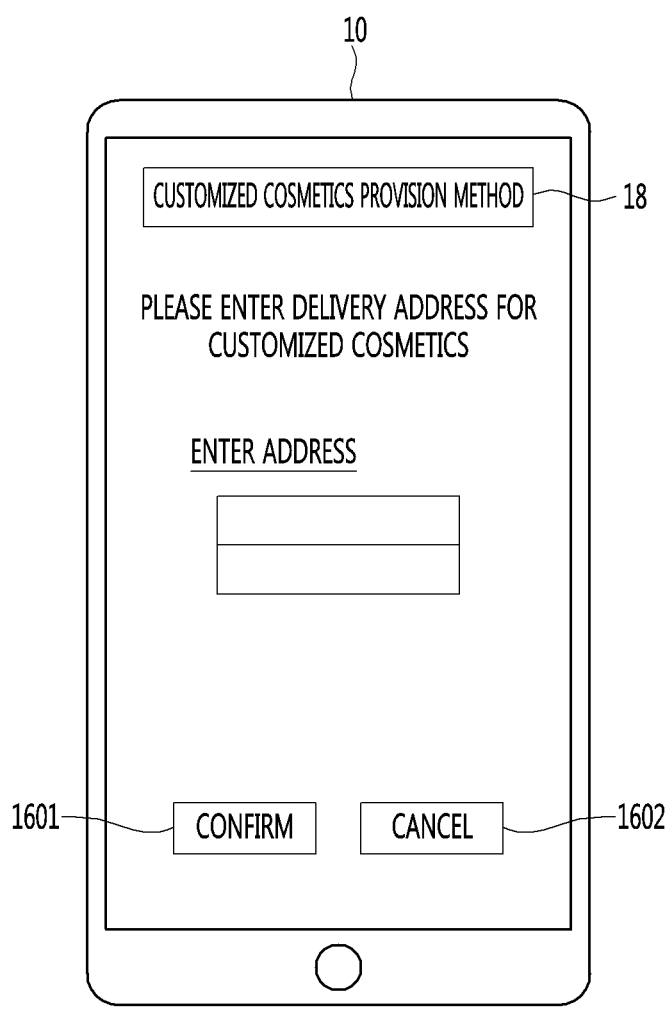
FIG. 15 is an illustrative screen for describing a method of delivering customized cosmetics according to an embodiment of the present invention.

FIG. 15 is an illustrative screen for describing a method of delivering customized cosmetics according to an embodiment of the present invention.

The diagnosis device 10 may receive a delivery address of the customized cosmetics through a screen as shown in FIG. 15.

When the input unit 11 of the diagnosis device 10 receives an instruction selecting an address input and confirm icon 1601, address information to deliver the cosmetics may be transmitted to the skin management server 20 or the manufacturing apparatus 30.

In this way, a user may transmit the address information to deliver the cosmetics to the skin management server 20 or the manufacturing apparatus 30 through the diagnosis device 10.

The skin management server 20 or the manufacturing apparatus 30 may control the customized cosmetics to be transmitted to the delivery address (S31).

Meanwhile, when the user does not intend to purchase the customized cosmetics at S17, the skin management server 20 may store customized cosmetics information in the storage unit 22 (S33).

Since the skin management server 20 stores the customized cosmetics information, there is an advantage that the customized cosmetics may be provided easily without re-diagnosing a skin condition later.

In addition, the skin management server 20 has an advantage that an improvement effect of the skin condition of the user may be recognized by comparing cosmetics recommended previously with cosmetics recommended next.

The present invention described above may be implemented as computer-readable codes in a medium on which a program is recorded. The computer-readable medium includes all kinds of recording devices in which computer-readable data is stored. Examples of the computer-readable medium include a hard disk drive (HDD), a solid state disk (SSD), a silicon disk drive (SDD), a ROM, a RAM, a CD-ROM, a magnetic tape, a floppy disk, and an optical data storage, etc. In addition, the computer may include a control unit of a diagnosis device, a control unit of a skin management server, or a control unit of a manufacturing apparatus. Accordingly, the above detailed description should not be construed in a limiting sense in all respects, and should be considered as examples. The scope of the present invention should be determined by rational interpretation of the appended claims, and encompasses all alterations falling within the equivalent scope of the appended claims.

What is claimed is:

1. A customized cosmetics provision system comprising:
a diagnosis device for diagnosing a skin condition, recommending customized cosmetics based on a diagnosis result of the skin condition, and transmitting information on recommended customized cosmetics to a manufacturing apparatus; and
the manufacturing apparatus that receives information on the customized cosmetics from the diagnosis device
wherein the diagnosis device comprises:
a measurement unit configured to measure surrounding environmental conditions and skin condition of a user; and
a controller configured to diagnose the skin condition of the user based on the measured surrounding environmental conditions and the skin condition of the user, and
wherein the controller is configured to obtain the surrounding environmental conditions and the skin condition of the user from the measurement unit, correct the skin condition of the user based on the measured surrounding environmental conditions, provide a diagnosis result including a skin stress due to exposure to harmful environment through diagnosing a corrected skin condition of the user, determine a mixing ratio of cosmetic materials through selecting one mixing ratio item from a plurality of mixing ratio items mixing the cosmetic materials based on the skin stress due to exposure to the harmful environment, and recommend the customized cosmetics based on the determined mixing ratio of the cosmetic materials,
wherein when determining mixing ratios, the controller is configured to determine the mixing ratios including a first mixing ratio of the cosmetic materials of a first group determining a first property, a second mixing ratio of the cosmetic materials of a second group determining a second property, a third mixing ratio of the cosmetic materials of a third group determining a third property, and a fourth mixing ratio of the first to third groups, and adjust each of the first to fourth mixing ratios based on the skin stress due to exposure to the harmful environment, and
wherein the manufacturing apparatus manufactures the customized cosmetics in response to the diagnosis device transmitting the mixing ratios of the cosmetic materials.

2. The customized cosmetics provision system of claim 1, wherein the diagnosis device obtains a skin image of the user's skin and outputs a message to re-diagnose the skin condition when a brightness of the skin image is less than or equal to a predetermined reference.

3. The customized cosmetics provision system of claim 1, wherein the diagnosis device includes at least one of a mobile terminal capable of diagnosing the skin condition of the user or a skin condition diagnosis device provided in a cosmetics sales place.

4. The customized cosmetics provision system of claim 3, wherein the customized cosmetics are provided at the cosmetics sales place closest to a current location of the mobile terminal when the diagnosis device is the mobile terminal.

5. The customized cosmetics provision system of claim 3, wherein the diagnosis device receives an input signal inputting a location, and the customized cosmetics are provided at the cosmetics sales place closest to an input location according to the input signal when the diagnosis device is the mobile terminal.

6. The customized cosmetics provision system of claim 5, wherein the diagnosis device receives a cosmetics receipt location change instruction and the customized cosmetics are provided at a cosmetics receipt location changed according to the instruction.

7. The customized cosmetics provision system of claim 3, wherein the diagnosis device receives an input signal inputting a delivery address, and the customized cosmetics are provided at a delivery address input according to the input signal when the diagnosis device is the mobile terminal.

8. The customized cosmetics provision system of claim 3, wherein the customized cosmetics are provided at the cosmetics sales place in which the skin condition is diagnosed when the diagnosis device is the skin condition diagnosis device provided at the cosmetics sales place.

9. The customized cosmetics provision system of claim 1, wherein the diagnosis device determines purchasing intention of the user corresponding to the recommended customized cosmetics, and when it is determined that there is the purchasing intention of the user corresponding to the customized cosmetics, transmits information on the customized cosmetics to the manufacturing apparatus.

10. The customized cosmetics provision system of claim 1, wherein the diagnosis device receives a correction signal that changes some or all of the recommended customized cosmetics.

11. The customized cosmetics provision system of claim 1, wherein the skin condition includes at least one of a skin color, a moisture content in skin, a sebum content in skin, elasticity, wrinkles, a presence of pigmentation, an amount of pores, keratin, a skin texture, sensitivity, a skin type, and skin trouble.

12. The customized cosmetics provision system of claim 1, the manufacturing apparatus comprising:
 at least one cartridge for containing a cosmetic material of the cosmetic materials;
 a cartridge support for accommodating the at least one cartridge;
 a motor mounted on one side of the cartridge support for moving a compression member; and
 the compression member configured to be moved by the motor for discharging the cosmetic material contained in the at least one cartridge when inserted into the cartridge.

13. The customized cosmetics provision system of claim 1, further comprising a skin management server configured to communicate with at least one of the diagnosis device and the manufacturing apparatus,
 wherein the skin management server comprises:
 a communication unit configured to receive a first diagnosis result corresponding to a first skin condition of a first user and information related to a first customized cosmetics corresponding to the first diagnosis result from the diagnosis device;
 a storage unit configured to store and map the first diagnosis result corresponding to the first skin condition of the first user and information related to a first customized cosmetics; and
 a control unit configure to obtain information related to a second customized cosmetics based on a second diagnosis result corresponding to a second skin condition of the first user and information related to a first customized cosmetics, when the second diagnosis result corresponding to the second skin condition of the first user is received.

14. The customized cosmetics provision system of claim 13, wherein the storage unit includes a cosmetics database storing information on customized cosmetics for each user, and
 wherein the control unit obtains information related to the second customized cosmetics and determines whether or not to output a screen for confirming whether information related to the second customized cosmetics is added to the cosmetic database.

15. The customized cosmetics provision system of claim 14, wherein the control unit obtains information on preferred cosmetics for each user based on the cosmetics database.

16. The customized cosmetics provision system of claim 13, wherein the storage unit includes a makeup image and a makeup database in which types of cosmetics used in the makeup image are mapped, and
 wherein the control unit extracts one of the makeup images in the makeup database based on a third diagnosis result corresponding to a third skin condition of the first user when the third diagnosis result corresponding to the third skin condition of the first user is received, and displays a screen to recommend the extracted makeup image through the diagnosis device.

17. The customized cosmetics provision system of claim 16, wherein the diagnosis device is configured to display cosmetics used in the extracted makeup image together with the extracted makeup image.

18. The customized cosmetics provision system of claim 1, wherein surrounding environmental conditions include at least one of temperature and humidity of a space in which the diagnosis device is located.

19. The customized cosmetics provision system of claim 1, wherein the skin stress due to the exposure to harmful environment is determined based on a degree of exposure to the harmful environment.

20. The customized cosmetics provision system of claim 1, wherein the cosmetic materials of the first group is a color base to provide a color to the customized cosmetics,
 wherein the cosmetic materials of the second group is a feeling base to provide a feel to the customized cosmetics, and
 wherein the cosmetic materials of the third group is an efficacy base to provide a functional efficacy to the customized cosmetics.

* * * * *